(12) United States Patent
Blum et al.

(10) Patent No.: US 7,034,034 B2
(45) Date of Patent: Apr. 25, 2006

(54) SUBSTITUTED 2-CYCLOHEXYL-4-PHENYL-1H-IMIDAZOLE DERIVATIVES

(75) Inventors: Charles A. Blum, Westbrook, CT (US); Harry L. Brielmann, Guilford, CT (US); Stephane De Lombaert, Madison, CT (US); Xiaozhang Zheng, Branford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 10/274,851

(22) Filed: Oct. 21, 2002

(65) Prior Publication Data

US 2003/0144290 A1    Jul. 31, 2003

Related U.S. Application Data

(60) Provisional application No. 60/348,974, filed on Oct. 23, 2001.

(51) Int. Cl.
*A61K 31/4164* (2006.01)
*A61K 31/4178* (2006.01)
*C07D 233/64* (2006.01)
*C07D 401/12* (2006.01)

(52) U.S. Cl. .............. 514/275; 514/341; 514/381; 514/393; 514/396; 544/331; 546/272.7; 548/345.1; 548/250; 548/302.1

(58) Field of Classification Search ............. 548/345.1, 548/250, 302.1; 546/272.7; 544/331; 514/275, 514/381, 341, 393, 396
See application file for complete search history.

(56) References Cited

U.S. PATENT DOCUMENTS

| | | | |
|---|---|---|---|
| 5,602,024 A | 2/1997 | Gerald et al. ............... 435/325 |
| 6,048,900 A | 4/2000 | Connell et al. ............ 514/663 |
| 6,372,743 B1 | 4/2002 | Darrow et al. | |
| 6,506,762 B1 | 1/2003 | Horvath et al. | |
| 6,566,367 B1 | 5/2003 | Bakthavatchalam et al. | |
| 6,696,445 B1 | 2/2004 | Horvath et al. | |
| 2001/0031474 A1 | 10/2001 | Kinrade et al | |
| 2003/0069246 A1 | 4/2003 | Darrow et al. | |

2004/0072847 A1    4/2004   Bakthavatchalam et al.

FOREIGN PATENT DOCUMENTS

| | | |
|---|---|---|
| EP | 1010691 | 6/2000 |
| WO | 97 20823 | 6/1997 |
| WO | 9719682 | 6/1997 |
| WO | 9720820 | 6/1997 |
| WO | 9720821 | 6/1997 |
| WO | 9720822 | 6/1997 |
| WO | 9720823 | 6/1997 |
| WO | 9746250 | 12/1997 |
| WO | 9825908 | 6/1998 |
| WO | 9827063 | 6/1998 |
| WO | 9840356 | 9/1998 |
| WO | 9932466 | 7/1999 |
| WO | 9948873 | 9/1999 |
| WO | 9948888 | 9/1999 |
| WO | 9955667 | 11/1999 |
| WO | 9964394 | 12/1999 |
| WO | 0027845 | 5/2000 |
| WO | 0068197 | 11/2000 |
| WO | WO 01/23387 | 4/2001 |
| WO | WO 01/23389 | 4/2001 |
| WO | 01 44201 | 6/2001 |
| WO | 0144201 | 6/2001 |
| WO | 01 62737 | 8/2001 |
| WO | WO 01/55103 | 8/2001 |
| WO | WO 02/48152 | 6/2002 |
| WO | WO 03/104255 | 12/2003 |

OTHER PUBLICATIONS

English Abstract of WO98/25908 dated Jun. 18,1998.
Engliah Abstract of WO98/27063 dated Jun. 25, 1998.
English Abstract of WO98/40356 dated Sep. 17, 1998.

*Primary Examiner*—Laura L. Stockton
(74) *Attorney, Agent, or Firm*—Lawson & Weitzen, LLP; Sonia K. Guterman

(57) ABSTRACT

Substituted 2-cyclohexyl-4-phenyl-1H-imidazole derivatives capable of modulating NPY5 receptor activity, are provided. Such compounds may be used to modulate NPY binding to NPY5 receptors in vivo or in vitro, and are particularly useful in the treatment of a variety of disorders (e.g., eating disorders such as obesity or bulimia, psychiatric disorders, diabetes and cardiovascular disorders such as hypertension) in humans, domesticated companion animals and livestock animals. Pharmaceutical compositions and methods for treating such disorders are provided, as are methods for using such compounds for detecting NPY5 receptors.

18 Claims, No Drawings

SEQUENCE LISTING

```
<160> NUMBER OF SEQ ID NOS: 17

<210> SEQ ID NO 1
<211> LENGTH: 21
<212> TYPE: DNA
<213> ORGANISM: Homo sapiens

<400> SEQUENCE: 1
ttttggttgc tgacaaatgt c                                              21

<210> SEQ ID NO 2
<211> LENGTH: 26
<212> TYPE: DNA
<213> ORGANISM: Homo sapiens

<400> SEQUENCE: 2
ccttggtaaa cagtgagaat tattac                                         26

<210> SEQ ID NO 3
<211> LENGTH: 1605
<212> TYPE: DNA
<213> ORGANISM: Homo sapiens

<400> SEQUENCE: 3
ccttctttaa tgaagcagga gcgaaaaaga caaattccaa agaggattgt tcagttcaag      60
ggaatgaaga attcagaata attttggtaa atggattcca atatggggaa taagaataag     120
ctgaacagtt gacctgcttt gaagaaacat actgtccatt tgtctaaaat aatctataac     180
aaccaaacca atcaaaatga attcaacatt attttcccag gttgaaaatc attcagtcca     240
ctctaatttc tcagagaaga atgcccagct tctggctttt gaaaatgatg attgtcatct     300
gcccttggcc atgatattta ccttagctct tgcttatgga gctgtgatca ttcttggtgt     360
ctctggaaac ctggccttga tcataatcat cttgaaacaa aaggagatga gaaatgttac     420
caacatcctg attgtgaacc tttccttctc agacttgctt gttgccatca tgtgtctccc     480
ctttacattt gtctacacat taatggacca ctgggtcttt ggtgaggcga tgtgtaagtt     540
gaatcctttt gtgcaatgtg tttcaatcac tgtgtccatt ttctctctgg ttctcattgc     600
tgtggaacga catcagctga ataatcaaccc tcgagggtgg agaccaaata atagacatgc     660
```

-continued

```
ttatgtaggt attgctgtga tttgggtcct tgctgtggct tcttctttgc ctttcctgat    720
ctaccaagta atgactgatg agccgttcca aaatgtaaca cttgatgcgt acaaagacaa    780
atacgtgtgc tttgatcaat ttccatcgga ctctcatagg ttgtcttata ccactctcct    840
cttggtgctg cagtatttg gtccactttg ttttatattt atttgctact tcaagatata    900
tatacgccta aaaggagaa acaacatgat ggacaagatg agagacaata agtacaggtc    960
cagtgaaacc aaaagaatca atatcatgct gctctccatt gtggtagcat ttgcagtctg   1020
ctggctccct cttaccatct ttaacactgt gtttgattgg aatcatcaga tcattgctac   1080
ctgcaaccac aatctgttat tcctgctctg ccacctcaca gcaatgatat ccacttgtgt   1140
caacccata ttttatgggt tcctgaacaa aaacttccag agagacttgc agttcttctt   1200
caacttttgt gatttccggt ctcgggatga tgattatgaa acaatagcca tgtccacgat   1260
gcacacagat gtttccaaaa cttctttgaa gcaagcaagc ccagtcgcat ttaaaaaaat   1320
caacaacaat gatgataatg aaaaaatctg aaactactta tagcctatgg tcccggatga   1380
catctgttta aaacaagca caacctgcaa catactttga ttacctgttc tcccaaggaa   1440
tgggggttgaa atcatttgaa aatgactaag attttcttgt cttgcttttt actgcttttg   1500
ttgtagttgt cataattaca tttggaacaa aaggtgtggg ctttggggtc ttctggaaat   1560
agttttgacc agacatcttt gaagtgcttt ttgtgaattt accag                    1605
```

<210> SEQ ID NO 4
<211> LENGTH: 384
<212> TYPE: PRT
<213> ORGANISM: Homo sapiens

<400> SEQUENCE: 4

```
Met Asn Ser Thr Leu Phe Ser Gln Val Glu Asn His Ser Val His Ser
  1               5                  10                  15

Asn Phe Ser Glu Lys Asn Ala Gln Leu Leu Ala Phe Glu Asn Asp Asp
             20                  25                  30

Cys His Leu Pro Leu Ala Met Ile Phe Thr Leu Ala Leu Ala Tyr Gly
         35                  40                  45

Ala Val Ile Ile Leu Gly Val Ser Gly Asn Leu Ala Leu Ile Ile Ile
     50                  55                  60

Ile Leu Lys Gln Lys Glu Met Arg Asn Val Thr Asn Ile Leu Ile Val
 65                  70                  75                  80

Asn Leu Ser Phe Ser Asp Leu Leu Val Ala Ile Met Cys Leu Pro Phe
                 85                  90                  95

Thr Phe Val Tyr Thr Leu Met Asp His Trp Val Phe Gly Glu Asn Met
            100                 105                 110

Cys Lys Leu Asn Pro Phe Val Gln Cys Val Ser Ile Thr Val Ser Ile
        115                 120                 125

Phe Ser Leu Val Leu Ile Ala Val Glu Arg His Gln Leu Ile Ile Asn
    130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205
```

```
Leu Ser Tyr Thr Thr Leu Leu Leu Val Leu Gln Tyr Phe Gly Pro Leu
    210                 215                 220
Cys Phe Ile Phe Ile Cys Tyr Phe Lys Ile Tyr Ile Arg Leu Lys Arg
225                 230                 235                 240
Arg Asn Asn Met Met Asp Lys Met Arg Asp Asn Lys Tyr Arg Ser Ser
                245                 250                 255
Glu Thr Lys Arg Ile Asn Ile Met Leu Leu Ser Ile Val Val Ala Phe
            260                 265                 270
Ala Val Cys Trp Leu Pro Leu Thr Ile Phe Asn Thr Val Phe Asp Trp
        275                 280                 285
Asn His Gln Ile Ile Ala Thr Cys Asn His Asn Leu Leu Phe Leu Leu
    290                 295                 300
Cys Ala Leu Thr Ala Met Ile Ser Thr Cys Val Asn Pro Ile Phe Tyr
305                 310                 315                 320
Gly Phe Leu Asn Lys Asn Phe Gln Arg Asp Ser Gln Phe Phe Phe Asn
                325                 330                 335
Phe Cys Asp Phe Arg Ser Arg Asp Asp Tyr Glu Thr Ile Ala Met
            340                 345                 350
Ser Thr Met His Thr Asp Val Ser Lys Thr Ser Leu Lys Gln Ala Ser
        355                 360                 365
Pro Val Ala Phe Lys Lys Ile Asn Asn Asn Asp Asp Asn Glu Lys Ile
    370                 375                 380

<210> SEQ ID NO 5
<211> LENGTH: 1069
<212> TYPE: DNA
<213> ORGANISM: Homo sapiens

<400> SEQUENCE: 5
ttttggttgc tgacaaatgt cttttattc caagcaggac tataatatgg atttagagct      60
cgacgagtat tataacaaga cacttgccac agagaataat actgctgcca ctcggaattc     120
tgatttccca gtctgggatg actataaaag cagtgtagat gacttacagt attttctgat     180
tgggctctat acatttgtaa gtcttcttgg ctttatgggg aatctactta ttttaatggc     240
tctcatgaaa aagcgtaatc agaagactac ggtaaacttc ctcataggca atctggcctt     300
ttctgatatc ttggttgtgc tgttttgctc acctttcaca ctgacgtctg tcttgctgga     360
tcagtggatg tttggcaaag tcatgtgcca tattatgcct tttcttcaat gtgtgtcagt     420
tttggtttca actttaattt taatatcaat tgccattgtc aggtatcata tgataaaaca     480
tcccatatct aataatttaa cagcaaacca tggctacttt ctgatagcta ctgtctggac     540
actaggtttt gccatctgtt ctccccttcc agtgtttcac agtcttgtgg aacttcaaga     600
aacatttggt tcagcattgc tgagcagcag gtatttatgt gttgagtcat ggccatctga     660
ttcatacaga attgcccttta ctatctcttt attgctagtt cagtatattc tgcccttagt     720
ttgtcttact gtaagtcata caagtgtctg catacgccta aaaggagaa acaacatgat      780
ggacaagatg agagacaata agtacaggtc agtagatct cgaagtgttt tctacagact     840
gaccatactg atattagtat ttgctgttag ttggatgcca ctacacctt tccatgtggt     900
aactgatttt aatgacaatc ttatttcaaa taggcatttc aagttggtgt attgcatttg     960
tcatttgttg ggcatgatgt cctgttgtct taatccaatt ctatatgggt tcttaataa    1020
tgggattaaa gctgatttag tgtcccttat acactgtctt catatgtaa               1069
```

<210> SEQ ID NO 6
<211> LENGTH: 1406
<212> TYPE: DNA
<213> ORGANISM: Homo sapiens

<400> SEQUENCE: 6

```
ttttggttgc tgacaaatgt cttttattc caagcaggac tataatatgg atttagagct      60
cgacgagtat tataacaaga cacttgccac agagaataat actgctgcca ctcggaattc     120
tgatttccca gtctgggatg actataaaag cagtgtagat gacttacagt attttctgat     180
tgggctctat acatttgtaa gtcttcttgg ctttatgggg aatctactta ttttaatggc     240
tctcatgaaa aagcgtaatc agaagactac ggtaaacttc ctcataggca atctggcctt     300
ttctgatatc ttggttgtgc tgttttgctc acctttcaca ctgacgtctg tcttgctgga     360
tcagtggatg tttggcaaag tcatgtgcca tattatgcct tttcttcaat gtgtgtcagt     420
tttggtttca actttaattt taatatcaat tgccattgtc aggtatcata tgataaaaca     480
tcccatatct aataatttaa cagcaaacca tggctacttt ctgatagcta ctgtctggac     540
actaggtttt gccatctgtt ctccccttcc agtgtttcac agtcttgtgg aacttcaaga     600
aacatttggt tcagcattgc tgagcagcag gtatttatgt gttgagtcat ggccatctga     660
ttcatacaga attgccttta ctatctcttt attgctagtt cagtatattc tgcccttagt     720
ttgtcttact gtaagtcata caagtgtctg cagaagtata agctgtggat tgtccaacaa     780
agaaaacaga cttgaagaaa atgagatgat caacttaact cttcatccat ccaaaaagag     840
tgggcctcag gtgaaactct ctggcagcca taatggagt tattcattca tcaaaaaaca     900
cagaagaaga tatagcaaga agacagcatg tgtgttacct gctccagaaa gaccttctca     960
agagaaccac tccagaatac ttccagaaaa ctttggctct gtaagaagtc agctctcttc    1020
atccagtaag ttcataccag gggtccccac ttgctttgag ataaaacctg aagaaaattc    1080
agatgttcat gaattgagag taaaacgttc tgttacaaga ataaaaaaga gatctcgaag    1140
tgttttctac agactgacca tactgatatt agtatttgct gttagttgga tgccactaca    1200
ccttttccat gtggtaactg attttaatga caatcttatt tcaaataggc atttcaagtt    1260
ggtgtattgc atttgtcatt tgttgggcat gatgtcctgt tgtcttaatc caattctata    1320
tgggtttctt aataatggga ttaaagctga tttagtgtcc cttatacact gtcttcatat    1380
gtaataattc tcactgttta ccaagg                                         1406
```

<210> SEQ ID NO 7
<211> LENGTH: 455
<212> TYPE: PRT
<213> ORGANISM: Homo sapiens

<400> SEQUENCE: 7

```
Met Ser Phe Tyr Ser Lys Gln Asp Tyr Asn Met Asp Leu Glu Leu Asp
  1               5                  10                  15

Glu Tyr Tyr Asn Lys Thr Leu Ala Thr Glu Asn Asn Thr Ala Ala Thr
             20                  25                  30

Arg Asn Ser Asp Phe Pro Val Trp Asp Asp Tyr Lys Ser Ser Val Asp
         35                  40                  45

Asp Leu Gln Tyr Phe Leu Ile Gly Leu Tyr Thr Phe Val Ser Leu Leu
     50                  55                  60

Gly Phe Met Gly Asn Leu Leu Ile Leu Met Ala Leu Met Lys Lys Arg
 65                  70                  75                  80

Asn Gln Lys Thr Thr Val Asn Phe Leu Ile Gly Asn Leu Ala Phe Ser
```

```
                85                  90                  95
Asp Ile Leu Val Val Leu Phe Cys Ser Pro Phe Thr Leu Thr Ser Val
            100                 105                 110
Leu Leu Asp Gln Trp Met Phe Gly Lys Val Met Cys His Ile Met Pro
            115                 120                 125
Phe Leu Gln Cys Val Ser Val Leu Val Ser Thr Leu Ile Leu Ile Ser
            130                 135             140
Ile Ala Ile Val Arg Tyr His Met Ile Lys His Pro Ile Ser Asn Asn
145                 150                 155                 160
Leu Thr Ala Asn His Gly Tyr Phe Leu Ile Ala Thr Val Trp Thr Leu
                165                 170                 175
Gly Phe Ala Ile Cys Ser Pro Leu Pro Val Phe His Ser Leu Val Glu
            180                 185                 190
Leu Gln Glu Thr Phe Gly Ser Ala Leu Leu Ser Ser Arg Tyr Leu Cys
        195                 200                 205
Val Glu Ser Trp Pro Ser Asp Ser Tyr Arg Ile Ala Phe Thr Ile Ser
    210                 215                 220
Leu Leu Leu Val Gln Tyr Ile Leu Pro Leu Val Cys Leu Thr Val Ser
225                 230                 235                 240
His Thr Ser Val Cys Arg Ser Ile Ser Cys Gly Leu Ser Trp Lys Glu
                245                 250                 255
Asn Arg Leu Glu Glu Asn Glu Met Ile Asn Leu Thr Leu His Pro Ser
            260                 265                 270
Lys Lys Ser Gly Pro Gln Val Lys Leu Ser Gly Ser His Lys Trp Ser
        275                 280                 285
Tyr Ser Phe Ile Lys Lys His Arg Arg Arg Tyr Ser Lys Lys Thr Ala
    290                 295                 300
Cys Val Leu Pro Ala Pro Glu Arg Pro Ser Gln Glu Asn His Ser Arg
305                 310                 315                 320
Ile Leu Pro Glu Asn Phe Gly Ser Val Arg Ser Gln Leu Ser Ser Ser
                325                 330                 335
Ser Lys Phe Ile Pro Gly Val Pro Thr Cys Phe Glu Ile Leu Pro Glu
            340                 345                 350
Glu Asn Ser Asp Val His Glu Leu Arg Val Lys Arg Ser Val Thr Arg
        355                 360                 365
Ile Lys Lys Arg Ser Arg Ser Val Phe Tyr Arg Leu Thr Ile Leu Ile
    370                 375                 380
Leu Val Phe Ala Val Ser Trp Met Pro Leu His Leu Phe His Val Val
385                 390                 395                 400
Thr Asp Phe Asn Asp Asn Leu Ile Ser Asn Arg His Phe Lys Leu Val
                405                 410                 415
Tyr Cys Ile Cys His Leu Leu Gly Met Met Ser Cys Cys Leu Asn Pro
            420                 425                 430
Ile Leu Tyr Gly Phe Leu Asn Asn Gly Ile Lys Ala Asp Leu Val Ser
        435                 440                 445
Leu Ile His Cys Leu His Met
450                 455

<210> SEQ ID NO 8
<211> LENGTH: 62
<212> TYPE: DNA
<213> ORGANISM: Homo sapiens

<400> SEQUENCE: 8
```

```
tacgcctaaa aaggagaaac aacatgatgg acaagatgag agacaataag tacaggtcca    60
gt                                                                   62

<210> SEQ ID NO 9
<211> LENGTH: 21
<212> TYPE: PRT
<213> ORGANISM: Homo sapiens

<400> SEQUENCE: 9

Ile Arg Leu Lys Arg Arg Asn Asn Met Met Asp Lys Met Arg Asp Asn
 1               5                  10                  15

Lys Tyr Arg Ser Ser
            20

<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: CHIMERIC
      Y1/Y5 PRIMER

<400> SEQUENCE: 10
tacgcctaaa aaggagaaac aacatgatgg acaagatgag agacaataag tacaggtcca    60
gta                                                                  63

<210> SEQ ID NO 11
<211> LENGTH: 71
<212> TYPE: DNA
<213> ORGANISM: Artificial Sequence
<220> FEATURE:
<223> OTHER INFORMATION: Description of Artificial Sequence: CHIMERIC
      Y1/Y5 PRIMER

<400> SEQUENCE: 11
gatctactgg acctgtactt attgtctctc atcttgtcca tcatgttgtt tctccttttt    60
aggcgtatgc a                                                         71

<210> SEQ ID NO 12
<211> LENGTH: 1500
<212> TYPE: DNA
<213> ORGANISM: Artificial Sequence
<220> FEATURE:
<223> OTHER INFORMATION: Description of Artificial Sequence: Y5/Y1
      CHIMERA

<400> SEQUENCE: 12
atgtcttttt attccaagca ggactataat atggatttag agctcgacga gtattataac    60
aagacacttg ccacagagaa taatactgct gccactcgga attctgattt cccagtctgg   120
gatgactata aaagcagtgt agatgactta cagtattttc tgattgggct ctatacattt   180
gtaagtcttc ttggctttat ggggaatcta cttattttaa tggctctcat gaaaaagcgt   240
aatcagaaga ctacgagtaaa cttcctcata ggcaatctgg ccttttctga tatcttggtt   300
gtgctgtttt gctcaccttt cacactgacg tctgtcttgc tggatcagtg gatgtttggc   360
aaagtcatgt gccatattat gccttttctt caatgtgtgt cagttttggt ttcaacttta   420 atttttaatat caattgccat tgtcaggtat catatgataa acatcccat atctaataat   480 ttaacagcaa accatggcta ctttctgata gctactgtct ggacactagg ttttgccatc   540
tgttctcccc ttccagtgtt tcacagtctt gtggaactta agaaacatt tggttcagca   600
```

```
ttgctgagca gcaggtattt atgtgttgag tcatggccat ctgattcata cagaattgcc    660
tttactatct ctttattgct agttcagtat attctgccct tagtttgtct tactgtaagt    720
catacaagtg tctgcagaag tataagctgt ggattgtcca acaaagaaaa cagacttgaa    780
gaaaatgaga tgatcaactt aactcttcat ccatccaaaa agagtgggcc tcaggtgaaa    840
ctctctggca gccataaatg gagttattca ttcatcaaaa aacacagaag aagatatagc    900
aagaagacag catgtgtgtt acctgctcca gaaagacctt ctcaagagaa ccactccaga    960
atacttccag aaaactttgg ctctgtaaga agtcagctct cttcatccag taagttcata   1020
ccaggggtcc ccacttgctt tgagataaaa cctgaagaaa attcagatgt tcatgaattg   1080
agagtaaaac gttctgttac aagaataaaa aagagatctc gaagtgtttt ctacagactg   1140
accatactga tattagtatt tgctgttagt tggatgccac tacacctttt ccatgtggta   1200
actgatttta atgacaatct tatttcaaat aggcatttca agttggtgta ttgcatttgt   1260
catttgttgg gcatgatgtc ctgttgtctt aatccaattc tatatgggtt tcttaataat   1320
ggaattcaga gagacttgca gttcttcttc aactttgtg atttccggtc tcgggatgat    1380
gattatgaaa caatagccat gtccacgatg cacacagatg tttccaaaac ttctttgaag   1440
caagcaagcc cagtcgcatt taaaaaaatc aacaacaatg atgataatga aaaaatctga   1500
```

```
<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: MUTAGENIC
      R1 PRIMER

<400> SEQUENCE: 13
gaacaaaaga attcagagag acttgcagtt c                                    31

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: MUTAGENIC
      R1 PRIMER

<400> SEQUENCE: 14
cagcttgaat tccattatta agaaaccc                                        28

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: PRIMER

<400> SEQUENCE: 15
gctactgtct ggacactagg ttttg                                           25

<210> SEQ ID NO 16
<211> LENGTH: 1201
<212> TYPE: DNA
<213> ORGANISM: Artificial Sequence
<220> FEATURE:
<223> OTHER INFORMATION: Description of Artificial Sequence: Y5/Y1
      CHIMERA

<400> SEQUENCE: 16
```

-continued

```
ttttggttgc tgacaaatgt cttttttattc caagcaggac tataatatgg atttagagct      60
cgacgagtat tataacaaga cacttgccac agagaataat actgctgcca ctcggaattc     120
tgatttccca gtctgggatg actataaaag cagtgtagat gacttacagt attttctgat     180
tgggctctat acatttgtaa gtcttcttgg ctttatgggg aatctactta ttttaatggc     240
tctcatgaaa aagcgtaatc agaagactac ggtaaacttc ctcataggca atctggcctt     300
ttctgatatc ttggttgtgc tgttttgctc acctttcaca ctgacgtctg tcttgctgga     360
tcagtggatg tttggcaaag tcatgtgcca tattatgcct tttcttcaat gtgtgtcagt     420
tttggtttca actttaattt taatatcaat tgccattgtc aggtatcata tgataaaaca     480
tcccatatct aataatttaa cagcaaacca tggctacttt ctgatagcta ctgtctggac     540
actaggtttt gccatctgtt ctccccttcc agtgtttcac agtcttgtgg aacttcaaga     600
aacatttggt tcagcattgc tgagcagcag gtatttatgt gttgagtcat ggccatctga     660
ttcatacaga attgcccttta ctatctcttt attgctagtt cagtatattc tgcccttagt     720
ttgtcttact gtaagtcata caagtgtctg catacgccta aaaggagaa acaacatgat     780
ggacaagatg agagacaata agtacaggtc cagtagatct cgaagtgttt tctacagact     840
gaccatactg atattagtat ttgctgttag ttggatgcca ctacacctttt ccatgtggt     900
aactgatttt aatgacaatc ttatttcaaa taggcatttc aagttggtgt attgcatttg     960
tcatttgttg ggcatgatgt cctgttgtct taatccaatt ctatatgggt ttcttaataa    1020
tggaattcag agagacttgc agttcttctt caacttttgt gatttccggt ctcgggatga    1080
tgattatgaa acaatagcca tgtccacgat gcacacagat gtttccaaaa cttctttgaa    1140
gcaagcaagc ccagtcgcat ttaaaaaaat caacaacaat gatgataatg aaaaaatctg    1200
a                                                                    1201
```

<210> SEQ ID NO 17
<211> LENGTH: 394
<212> TYPE: PRT
<213> ORGANISM: Artificial Sequence
<220> FEATURE:
<223> OTHER INFORMATION: Description of Artificial Sequence: Y5/Y1
      CHIMERA

<400> SEQUENCE: 17

```
Met Ser Phe Tyr Ser Lys Gln Asp Tyr Asn Met Asp Leu Glu Leu Asp
  1               5                  10                  15

Glu Tyr Tyr Asn Lys Thr Leu Ala Thr Glu Asn Asn Thr Ala Ala Thr
             20                  25                  30

Arg Asn Ser Asp Phe Pro Val Trp Asp Asp Tyr Lys Ser Ser Val Asp
         35                  40                  45

Asp Leu Gln Tyr Phe Leu Ile Gly Leu Tyr Thr Phe Val Ser Leu Leu
     50                  55                  60

Gly Phe Met Gly Asn Leu Leu Ile Leu Met Ala Leu Met Lys Lys Arg
 65                  70                  75                  80

Asn Gln Lys Thr Thr Val Asn Phe Leu Ile Gly Asn Leu Ala Phe Ser
                 85                  90                  95

Asp Ile Leu Val Val Leu Phe Cys Ser Pro Phe Thr Leu Thr Ser Val
            100                 105                 110

Leu Leu Asp Gln Trp Met Phe Gly Lys Val Met Cys His Ile Met Pro
        115                 120                 125

Phe Leu Gln Cys Val Ser Val Leu Val Ser Thr Leu Ile Leu Ile Ser
    130                 135                 140
```

```
Ile Ala Ile Val Arg Tyr His Met Ile Lys His Pro Ile Ser Asn Asn
145                 150                 155                 160

Leu Thr Ala Asn His Gly Tyr Phe Leu Ile Ala Thr Val Trp Thr Leu
                165                 170                 175

Gly Phe Ala Ile Cys Ser Pro Leu Pro Val Phe His Ser Leu Val Glu
                180                 185                 190

Leu Gln Glu Thr Phe Gly Ser Ala Leu Leu Ser Ser Arg Tyr Leu Cys
            195                 200                 205

Val Glu Ser Trp Pro Ser Asp Ser Tyr Arg Ile Ala Phe Thr Ile Ser
        210                 215                 220

Leu Leu Leu Val Gln Tyr Ile Leu Pro Leu Val Cys Leu Thr Val Ser
225                 230                 235                 240

His Thr Ser Val Cys Ile Arg Leu Lys Arg Arg Asn Asn Met Met Asp
                245                 250                 255

Lys Met Arg Asp Asn Lys Tyr Arg Ser Ser Arg Ser Arg Ser Val Phe
            260                 265                 270

Tyr Arg Leu Thr Ile Leu Leu Ile Val Pro Ala Val Ser Trp Met Pro
        275                 280                 285

Leu His Leu Phe His Val Val Thr Ala Phe Asn Asp Asn Leu Ile Ser
290                 295                 300

Asn Arg His Phe Lys Leu Val Tyr Cys Ile Cys His Leu Leu Gly Met
305                 310                 315                 320

Met Ser Cys Cys Leu Asn Pro Ile Leu Tyr Gly Phe Leu Asn Asn Gly
                325                 330                 335

Ile Gln Arg Asp Leu Gln Phe Phe Asn Phe Cys Asp Phe Arg Ser
            340                 345                 350

Arg Asp Asp Asp Tyr Glu Thr Ile Ala Met Ser Thr Met His Thr Asp
            355                 360                 365

Val Ser Lys Thr Ser Leu Lys Gln Ala Ser Pro Val Ala Phe Lys Lys
370                 375                 380

Ile Asn Asn Asn Asp Asp Asn Glu Lys Ile
385                 390
```

SUBSTITUTED 2-CYCLOHEXYL-4-PHENYL-1H-IMIDAZOLE DERIVATIVES

This application claims the benefit of U.S. Provisional Patent Application Ser. No. 60/348,974, filed on Oct. 23, 2001, and incorporates the same by reference.

FIELD OF THE INVENTION

This invention relates generally to substituted 2-cyclohexyl-4-phenyl-1H-imidazole derivatives that are modulators of mammalian neuropeptide $Y_5$ (NPY5) receptors, and to the use of such compounds for treating a variety of physiological disorders associated with NPY5 receptor activation, such as feeding disorders, psychiatric disorders and cardiovascular diseases. The invention further relates to the use such compounds as probes for the detection and localization of NPY5 receptors.

BACKGROUND OF THE INVENTION

Neuropeptide Y (NPY) is a 36 amino acid peptide that mediates a variety of physiological effects in humans and other mammals. This peptide was first isolated by Tatemoto et al. (*Nature* (1982) 296:659) and subsequently found to be largely conserved across mammalian species. It belongs to a large family of peptides that includes, among others, peptide YY (PYY) and pancreatic peptide (PP). NPY is the most abundant peptide in the mammalian brain, and is also present in sympathetic neurons. In addition, NPY-containing fibers have been found in peripheral tissues, such as around the arteries in the heart, the respiratory tract, the gastrointestinal tract and the genitourinary tract.

Central injection of NPY elicits a multitude of physiological responses, such as stimulation of feeding, increase in fat storage, elevation of blood sugar and insulin, anxiolytic behaviors, reduction in locomotor activity, hormone release, increase in blood pressure, reduction in body temperature and catalepsy. In the cardiovascular system, NPY appears to be involved in the regulation of coronary tone. These effects are selectively mediated by various NPY receptors, which currently include the $Y_1$, $Y_2$, $Y_3$, $Y_4$, $Y_5$ and $Y_6$ subtypes, as well as the hypothetical $Y_{1-like}$ subtype (e.g., Wahlestedt and Reis (1993) *Ann. Rev. Pharmacol. Toxicol.* 33:309; Gehlert and Hipskind (1995) *Curr. Pharm. Design*, 1:295; Michel et al. (1998) *Pharmacol. Rev.* 50:143).

The $Y_5$ receptor subtype (e.g., U.S. Pat. No. 5,602,024) appears to be involved in appetite regulation, including the modulation of food intake and energy expenditure. In addition, studies of seizure-prone mice have suggested that the $NPY_5$ receptor may have an anti-epileptic activity in the control of limbic seizures. $NPY_5$-like receptors have also been implicated in attenuation of morphine withdrawal symptoms, enhancement of diuresis and natriuresis, lowering of blood glucose, inhibition of luteinizing hormone secretion, and reduction of acetylcholine release in the ileum. See, for example, Hu et al.(1996) *J. Biol. Chem.,* 271:26315–19; Gerald et al.(1996) *Nature,* 382:168–71; Blomquist et al. (1997) *TINS,* 20: 294–98.

Selective peptide agonists and antagonists have been identified for most of the NPY receptor subtypes. Peptides, however, generally have serious shortcomings for therapeutic use including, poor metabolic stability, low oral bioavailability and poor brain permeability. To date, few non-peptide antagonists have been reported. WO 01/44201 describes certain substituted imidazole NPY receptor antagonists, but additional antagonists with improved properties are needed as therapeutic agents for the treatment of physiological disorders associated with NPY5 receptor activation, such as feeding disorders (e.g., obesity and bulimia), psychiatric disorders, diabetes and cardiovascular diseases (such as hypertension). The present invention fulfills this need, and provides further related advantages.

SUMMARY OF THE INVENTION

The present invention provides NPY5 receptor modulators that inhibit or enhance NPY binding to NPY5 receptor. Such modulators generally comprise a substituted 2-cyclohexyl-4-phenyl-1H-imidazole derivative characterized by the formula:

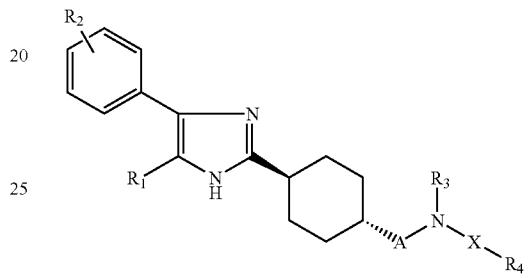

Formula I or a pharmaceutically acceptable salt thereof. Within Formula I, $R_1$ represents (within certain embodiments) hydrogen, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, halo($C_1$–$C_8$)alkyl, halo($C_1$–$C_8$) alkoxy, hydroxy($C_1$–$C_8$)alkyl, hydroxy($C_1$–$C_8$)alkoxy, mono or di($C_1$–$C_8$)alkyl amino, $C_1$–$C_8$ alkanoyl, $C_1$–$C_8$ alkoxycarbonyl, $C_1$–$C_8$ alkanoyloxy, $C_1$–$C_8$ carbonate, $C_1$–$C_8$ carbamate, 13 COOH, —$SO_2NH_2$, mono or dialkylsulfonamido, —C(O)$NH_2$ or mono or di($C_1$–$C_8$)alkylcarboxamido; within other embodiments, $R_1$ is taken together with an $R_2$ substituent (preferably in an ortho position) to represent a 5-to 7-member carbocyclic or heterocyclic ring that is fused to the phenyl and imidazole rings of formula I. $R_1$ is preferably hydrogen, $C_1$–$C_6$ alkyl or a group that, taken with $R_2$, forms a six-membered ring.

$R_2$ of Formula I represents 0 to 5 ring substitutents, each substituent independently selected from hydrogen, halogen, hydroxyl, amino, cyano, nitro, $C_1$–$C_8$ alkyl, $C_2$–$C_8$ alkenyl, $C_2$–$C_8$ alkynyl, $C_1$–$C_6$ alkoxy, $C_1$–$C_8$ alkylthio, halo($C_1$–$C_8$) alkyl, halo($C_1$–$C_8$)alkoxy, hydroxy($C_1$–$C_8$)alkyl, hydroxy ($C_1$–$C_8$)alkoxy, mono or di($C_1$–$C_8$) alkyl amino, $C_1$–$C_8$ alkanoyl, $C_1$–$C_8$ alkanoyloxy, $C_1$–$C_8$ carbonate, $C_1$–$C_8$ carbamate, $C_1$–$C_8$ alkoxycarbonyl, —COOH, —$SO_2NH_2$, mono and dialkylsulfonamido, —C(O)$NH_2$, mono and di($C_1$–$C_8$)alkylcarboxamido, and substituents that (taken together with $R_1$) form a 5- to 7-member carbocyclic or heterocyclic ring that is fused to the benzene and imidazole rings of Formula I.

A represents —C(O)— or —($CH_2$)$_n$—, wherein n is an integer ranging from 1 to 3. Within certain preferred embodiments A is —C(O)— or —$CH_2$—.

Within Formula I, $R_3$ represents (i) hydrogen; (ii) $C_1$–$C_8$ alkyl, optionally substituted with from 1 to 6 substituents that are independently selected from halogen, hydroxyl, carbocyclic groups and heterocyclic groups, wherein each carbocyclic or heterocyclic group contains from 3 to 10 ring members; or (iii) a bond to $R_4$, forming a heterocyclic group having from 1 to 3 fused or pendant rings, each ring containing from 5 to 10 ring members, wherein each ring is optionally substituted by from 1 to 5 substituents that are independently selected from halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, hydroxy, amino, mono or di($C_1$–$C_8$)alkyl amino, halo($C_1$–$C_8$)alkyl, halo($C_1$–$C_8$)alkoxy, hydroxy($C_1$–$C_8$) alkyl, hydroxy($C_1$–$C_8$)alkoxy $C_2$–$C_8$ alkanoyl, $C_1$–$C_8$ alkoxycarbonyl, —COOH, —$SO_2NH_2$, mono or dialkylsulfonamido, —C(O)$NH_2$ and mono and di($C_1$–$C_8$)alkylcarboxamido. Within certain preferred embodiments, $R_3$ is hydrogen, methyl, ethyl or propyl.

X of formula I represents a bond, —S(O)$_2$—, —C(O)— or —NHC(O)—.

Within Formula I, $R_4$ (i) represents hydrogen; (ii) represents $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_1$–$C_8$ carbonate, halo($C_1$–$C_8$) alkyl, halo($C_1$–$C_8$)alkoxy, hydroxy($C_1$–$C_8$)alkyl, hydroxy ($C_1$–$C_8$)alkoxy, $C_1$–$C_8$ alkanone or $C_1$–$C_8$ alkyl ether, optionally substituted with from 1 to five substituents that are independently selected from halogen, hydroxyl, carbocyclic groups and heterocyclic groups, wherein each carbocyclic or heterocyclic group contains from 5 to 10 ring members; or (iii) alone or taken together with $R_3$, X and the N to which $R_3$ is bonded, represents a carbocyclic or heterocyclic group having from 1 to 3 fused or pendant rings, each ring containing from 5 to 10 ring members, wherein each ring is optionally substituted by from 1 to 5 substituents that are independently selected from halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_1$–$C_8$ carbonate, $C_1$–$C_8$ carbamate, $C_1$–$C_8$ alkylthio, hydroxy, amino, mono or di($C_1$–$C_8$)alkyl amino, halo($C_1$–$C_8$)alkyl, halo($C_1$–$C_8$) alkoxy, hydroxy($C_1$–$C_8$)alkyl, hydroxy($C_1$–$C_8$)alkoxy $C_2$–$C_8$ alkanoyl, $C_1$–$C_8$ alkoxycarbonyl, —COOH, —$SO_2NH_2$, mono or dialkylsulfonamido, —C(O)$NH_2$ and mono or di($C_1$–$C_8$)alkylcarboxamido. Within certain preferred embodiments, $R_4$ is (i) an aromatic group selected from phenyl, benzyl, phenoxyl, benzoxyl, phenylethanonyl, pyrimidin-2-yl, tetrahydropyran-2-yl, 2-hydroxy-indan-1-yl, tetrazolyl, pyrimidin-2-yl, pyrimidin-4-yl, pyrimidin-5-yl, pyridin-2-yl, pyridin-3-yl and pyridin-4-yl, wherein the group is optionally substituted by from 1 to 3 substituents independently selected from hydroxyl, halogen and $C_1$–$C_6$ alkyl; (ii) a non-aromatic group selected from hydrogen, $C_1$–$C_6$ alkyl, $C_1$–$C_6$ alkoxy, $C_1$–$C_8$ alkanoyloxy, $C_1$–$C_8$ carbonate, halo($C_1$–$C_6$)alkyl, halo($C_1$–$C_6$)alkoxy, hydroxy ($C_1$–$C_6$)alkyl, hydroxy($C_1$–$C_6$)alkoxy, $C_1$–$C_6$ alkanone or $C_1$–$C_6$ alkyl ether; or (iii) taken with X, $R_3$ and the N bonded to $R_3$ to form a heterocyclic group selected from tetrazolyl, morpholin-4-yl, pyrimidin-2-yl, pyridin-2-yl, pyridin-3-yl and pyridin-4-yl, piperdin-1-yl, pyrrolidin-1-yl, each of which is optionally substituted with from 1 to 3 ring substitutents that are independently selected from halogen, $C_1$–$C_6$ alkyl, $C_1$–$C_6$ alkoxyl, hydroxyl, halo($C_1$–$C_6$)alkyl and halo($C_1$–$C_6$)alkoxyl.

Within certain preferred embodiments, $R_2$ is a meta-substituted trifluoromethyl, halogen or cyano. In other words, within such embodiments, the compound further satisfies Formula II, and $R_2$ is trifluoromethyl, halogen or cyano.

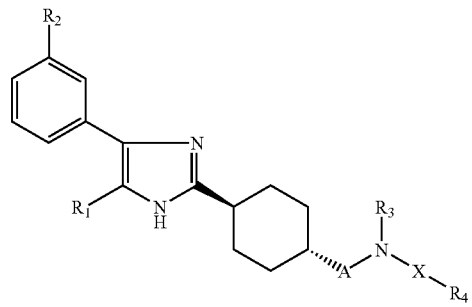

Formula II

Within certain preferred embodiments, X is $SO_2$, $R_3$ is hydrogen and $R_4$ is a group selected from phenyl, pyridyl and pyrimidyl, wherein the group is optionally substituted with from 1 to 3 substituents independently selected from hydroxyl, halogen and $C_1$–$C_6$ alkyl. Within other preferred embodiments, A is —$CH_2$—, X is CO, $R_3$ is hydrogen and $R_4$ is $C_1$–$C_6$ alkyl, $C_1$–$C_6$ alkoxyl, halo($C_1$–$C_6$)alkyl or halo($C_1$–$C_6$)alkoxyl. Within still further preferred embodiments, A is CO, X is —NHC(O)—, $R_3$ is hydrogen and $R_4$ is $C_1$–$C_6$ alkyl. Yet other preferred embodiments include compounds in which A is CO, X is a bond, $R_3$ is hydrogen or $C_1$–$C_6$ alkyl, and $R_4$ is $C_1$–$C_6$ alkyl, halo($C_1$–$C_6$)alkyl, hydroxy($C_1$–$C_6$)alkyl, or an aromatic group selected from phenyl, pyrimidin-2-yl, indan-1-yl, wherein the group is optionally substituted with from 1 to 3 substituents independently selected from hydroxyl, halogen, $C_1$–$C_6$ alkyl, hydroxy($C_1$–$C_6$)alkyl and $C_1$–$C_6$ alkanone.

Within certain embodiments, substituted 2-cyclohexyl-4-phenyl-1H-imidazole derivatives provided herein include: (a) 2-Chloro-N-{4-[4-(3-trifluoromethyl-phenyl)-1H-imidazol-2-yl]-cyclohexanecarbonyl}-benzene sulfonamide; (b) 4-[4-(3-Trifluoromethyl-phenyl)-1H-imidazol-2-yl]-cyclohexanecarboxylic acid(2-hydroxy-propyl)-methyl-amide; (c) 4-[4-(3-Trifluoromethyl-phenyl)-1H-imidazol-2-yl]-cyclohexane carboxylic acid(2-oxo-2-phenyl-ethyl)-amide; (d) Pyridine-3-sulfonicacid {4-[4-(3-trifluoro-methyl-phenyl)-1H-imidazol-2-yl]-cyclohexylmethyl}-amide; (e) 4-[4-(3-Trifluoromethyl-phenyl)-1H-imidazol-2-yl]-cyclohexanecarboxylic acid(2-hydroxy-2-phenyl-ethyl)-amide; (f) 1-{4-[4-(3-Trifluoromethyl-phenyl)-1H-imidazol-2-yl]-cyclohexylmethyl}-1H-tetrazole; (g) N-{4-[4-(3-Trifluoromethyl-phenyl)-1H-imidazol-2-yl]-cyclohexylmethyl}-benzenesulfonamide; (h) 4-[4-(3-Trifluoromethyl-phenyl)-1H-imidazol-2-yl]-cyclohexanecarboxylic acid(2-hydroxy-indan-1-yl)-amide; (i) {4-[4-(3-Chloro-phenyl)-1H-imidazol-2-yl]-cyclohexylmethyl}-carbamic acid ethyl ester; (j) Cyclopentyl-{4-[4-(3-trifluoromethyl-phenyl)-1H-imidazol-2-yl]-cyclohexylmethyl}-amine; (k) N-{4-[4-(4-Bromo-phenyl)-1H-imidazol-2-yl]-cyclohexylmethyl}-2,2,2-trifluoro-acetamide; (l) N-{4-[4-(3-trifluoromethyl-phenyl)-1H-imidazol-2-yl]-cyclohexanecarbonyl}-benzene sulfonamide; (m) Pyrimidin-2-yl-{4-[4-(3-trifluoromethyl-phenyl)-1H-imidazol-2-yl]-cyclohexylmethyl}-amine; (n) 4-[4-(3-Bromo-phenyl)-1H-imidazol-2-yl]-cyclohexanecarboxylic acid N-acetyl-hydrazide; (o) 4,N-Dimethyl-N-{4-[4-(3-trifluoromethyl-phenyl)-1H-imidazol-2-yl]-cyclohexanecarbonyl}-benzene sulfonamide; (p) N-{4-[4-(3-Trifluoromethyl-phenyl)-1H-imidazol-2-yl]-cyclohexylmethyl}-acetamide; (q) Benzenesulfinic acid {4-[4-(3-chloro-phenyl)-1H-imidazol-2-yl]- cyclohexylmethyl}-amide; (r) 4-[4-(3-Trifluoromethyl-phenyl)-1H-imidazol-2-yl]-cyclohexanecarboxylic acid(2-hydroxy-1,1-dimethyl-ethyl)-amide; (s) 4-Hydroxy-N-{4-[4-(3-trifluoromethyl-phenyl)-1H-imidazol-2-yl]-cyclohexylmethyl}-butyramide; (t) 4-methyl-N-{4-[4-(3-trifluoromethyl-phenyl)-1H-imidazol-2-yl]-cyclohexanecarbonyl}-benzene sulfonamide; (u) N-{4-[4-(3-Bromo-phenyl)-1H-imidazol-2-yl]-cyclohexylmethyl}-trifluoroacetamide; (v) 4-[4-(3-Trifluoromethyl-phenyl)-1H-imidazol-2-yl]-cyclohexanecarboxylic acid (2-hydroxy-propyl)-amide; (w) N-{4-[5-methyl-4-(3-trifluoromethyl-phenyl)-1H-imidazol-2-yl]-cyclohexylmethyl}-acetamide; (x) 2,2,2-Trifluoro-N-{4-[4-(4-methoxy-phenyl)-1H-imidazol-2-yl]-cyclohexylmethyl}-acetamide; (y) 4-Chloro-N-{4-[4-(3-trifluoromethyl-phenyl)-1H-imidazol-2-yl]-cyclo-hexanecarbonyl}-benzene sulfonamide; (z) N-[4-(8-Methoxy-4,5-dihydro-3H-naphtho[1,2-d]imidazol-2-yl)-cyclohexylmethyl]-benzenesulfonamide; (aa) 4-[4-(3-Bromo-phenyl)-1H-imidazol-2-yl]-cyclohexanecarboxylic acid pyrimidin-2-ylamide; (bb) N-Methyl-N-{4-[4-(3-trifluoromethyl-phenyl)-1H-imidazol-2-yl]-cyclohexylmethyl}-benzenesulfonamide; (cc) N-{4-[4-(3-Bromo-phenyl)-1H-imidazol-2-yl]-cyclohexylmethyl}-acetamide; (dd) 5-Methyl-pyridine-2-sulfonic acid {4-[4-(3-trifluoromethyl-phenyl)-1H-imidazol-2-yl]-cyclohexanecarbonyl}-amide; (ee) 4-[4-(3-Trifluoromethyl-phenyl)-1H-imidazol-2-yl]-cy-clohexanecarboxylic acid (1-hydroxymethyl-2-methyl-propyl)-amide; (ff) {4-[5-Methyl-4-(3-trifluoromethyl-phenyl)-1H-imidazol-2-yl]-cyclohexylmethyl}-carbamic acid benzyl ester; (gg) [4-(8-Methoxy-4,5-dihydro-3H-naphtho[1,2-d]imidazol-2-yl)-cyclohexylmethyl]-carbamic acid benzyl ester; (hh) 4-[4-(3-Trifluoromethyl-phenyl)-1H-imidazol-2-yl]-cyclohexanecarboxylic acid N-acetyl-hydrazide; (ii) 2,2,2-Trifluoro-N-[4-(4-phenyl-1H-imidazol-2-yl]-cyclohexylmethyl]-acetamide; and (jj) 2,2,2-Trifluoro-N-{4-[4-(3-trifluoromethyl-phenyl)-1H-imidazol-2-yl]-cyclohexylmethyl}-acetamide.

Within certain embodiments, substituted 2-cyclohexyl-4-phenyl-1H-imidazole derivatives provided herein exhibit a $K_i$ of 1 micromolar or less, 100 nanomolar or less, or 10 nanomolar or less in an NPY5 receptor ligand binding assay as provided in Example 11. The ligand (e.g., NPY or PYY) in such assays may be radiolabeled.

Within certain aspects, an NPY5 receptor modulator provided herein comprises a 2-cyclohexyl-4-phenyl-1H-imidazole derivative as described above associated with (i.e., linked to or combined with) a targeting moiety or carrier.

Within further aspects, the present invention provides pharmaceutical compositions comprising a compound or modulator as described above in combination with a physiologically acceptable carrier or excipient. Within certain embodiments, a pharmaceutical composition provided herein may further comprise one or more additional active agents (i.e., drugs). Pharmaceutical compositions provided herein may be formulated, for example, as an injectable fluid, an aerosol, a cream, a gel, a pill, a capsule, a syrup or a transdermal patch.

The present invention further provides, within other aspects, methods for treating a disease or disorder associated with NPY5 receptor activation, comprising administering to a patient in need of such treatment an effective amount of a compound or modulator as described above. Such diseases and disorders include, for example, eating disorders (e.g., obesity and bulimia nervosa), psychiatric disorders, cardiovascular disorders and diabetes. The compound or modulator may be administered orally, or via another means such as intranasally, intravenously or topically. Within certain embodiments, the patient is a human.

Within further aspects, the present invention provides compounds as described above, wherein the compounds are radiolabeled.

Methods are provided, within other aspects, for determining the presence or absence of NPY5 receptor in a sample, comprising the steps of: (a) contacting a sample with an agent comprising a compound as described above under conditions that permit binding of the agent to NPY5 receptor; and (b) detecting a level of agent bound to NPY5 receptor. Within certain embodiments, the agent is a radiolabeled compound, and the step of detection comprises the steps of: (i) separating unbound agent from bound agent; and (ii) detecting the presence or absence of bound agent in the sample. Detection may be achieved, for example, using autoradiography.

The present invention further provides, within other aspects, methods for modulating binding of NPY to NPY5 receptor. Certain such methods are performed in vitro, and comprise contacting NPY5 receptor with a compound or modulator as described above under conditions and in an amount sufficient to detectably modulate NPY binding to NPY5 receptor. Other such methods may be performed in vivo, and comprise contacting cells expressing NPY5 receptor with a compound or modulator as described above in an amount sufficient to detectably modulate NPY binding to cells expressing a cloned NPY5 receptor in vitro. Modulating of NPY binding may be determined, for example, using a ligand binding assay as provided in Example 11.

Methods are further provided for modulating binding of NPY to NPY5 receptor in a patient, comprising administering to a patient (i.e., a human or non-human animal) a compound or modulator as described above. Patients may include, for example, companion animals such as dogs.

Within certain embodiments of the above methods, the modulation is inhibition and/or the NPY5 receptor is a human NPY5 receptor.

Within further aspects, the present invention provides methods for modulating the signal-transducing activity of NPY5 receptor, comprising contacting an NPY5 receptor, either in vivo or in vitro, with a sufficient amount of an NPY5 receptor modulator, under conditions suitable for binding of NPY to NPY5 receptor.

Also provided by the present invention are packaged pharmaceutical preparations, comprising: (a) a pharmaceutical composition as described above in a container; and (b) instructions for using the composition to treat a patient suffering from a disease or disorder associated with NPY5 receptor activation. Such disorders include, for example, eating disorders, psychiatric disorders, cardiovascular disorders (such as hypertension) and diabetes.

These and other aspects of the present invention will become apparent upon reference to the following detailed description. All references disclosed herein are hereby incorporated by reference in their entirety as if each was incorporated individually.

DETAILED DESCRIPTION

As noted above, the present invention provides NPY5 receptor modulators comprising small molecule NPY5 receptor ligands that are 2-cyclohexyl-4-phenyl-1H-imidazole derivatives. Such modulators may be used in vitro or in vivo, to inhibit or enhance NPY binding to NPY5 receptor in a variety of contexts, discussed in further detail below.

Definitions

Prior to setting forth the invention in detail, it may be helpful to provide definitions of certain terms to be used herein. Compounds of the present invention are generally described using standard nomenclature. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Where a compound exists in various tautomeric forms, the invention is not limited to any one of the specific tautomers, but rather includes all tautomeric forms. Certain compounds are described herein using a general formula that includes variables. Unless otherwise specified, each variable within such a formula is defined independently of other variables.

As used herein, "$C_1$–$C_8$ alkyl" refers to straight or branched chain alkyl groups or cycloalkyl groups having 1–8 carbon atoms such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, cyclopropyl, cyclopropylmethyl, cyclopentyl, cyclohexyl, cycloheptyl and norbornyl. A $C_1$–$C_8$ alkyl substituent may be bonded to an atom within a molecule of interest via any chemically suitable portion of the $C_1$–$C_8$ alkyl group. Preferred alkyl groups are $C_1$–$C_6$ alkyl groups, especially methyl, ethyl, propyl, butyl, cyclopropyl, cyclopropylmethyl, cyclopentyl and cyclohexyl. Particularly preferred alkyl groups are methyl and ethyl. Similarly, "$C_2$–$C_8$ alkenyl" refers to straight or branched chain alkene groups or cycloalkene groups having 2 to 8 carbon atoms. Within an alkenyl group, one or more unsaturated carbon-carbon double bonds are present, and may occur at any stable point along the chain (e.g., ethenyl, allyl and isopropenyl). "$C_2$–$C_8$ alkynyl" refers to straight or branched chain alkyne groups having 2 to 8 carbon atoms. Within such a group, one or more unsaturated carbon-carbon triple bonds are present, and may occur at any stable point along the chain (e.g., ethynyl and propargyl). A "stable point" is bond that, when unsaturated, results in a chemically stable compound (i.e., a compound that can be isolated, characterized and tested for biological activity).

By "$C_3$–$C_{10}$ cycloalkyl" is meant alkyl groups having 3–10 carbon atoms forming a mono-, bi-, or polycyclic ring system, such as, for example, cyclopropyl, cyclobutyl, cyclopentyl, cyclohexyl, cycloheptyl and norbornyl. Cycloalkyl groups having 3–8 ring atoms are also encompassed by the term "$C_1$–$C_8$ alkyl," but the term "$C_3$–$C_{10}$ cycloalkyl" further encompasses 9- and 10-membered rings. Similarly, "cycloalkenyl" or "$C_3$–$C_{10}$ cycloalkenyl" refers to hydrocarbon groups having 3–10 carbon atoms forming a mono-, bi, or polycyclic ring system and containing one or more carbon-carbon double bonds which may occur at any stable point in the ring (e.g., cyclopentenyl, cyclohexenyl or cycloheptenyl).

The term "(cycloalkyl)alkyl" or "($C_3$–$C_{10}$)cycloalkyl($C_1$–$C_8$)alkyl" refers to a straight or branched alkyl substituent having of 1 to 8 carbon atoms that is attached to a mono-, bi, or polycyclic ring system having 3–10 carbon atoms (e.g., cyclopropylmethyl, cyclobutylmethyl, cyclopentylmethyl, cyclohexylmethyl and cycloheptylmethyl).

"$C_2$–$C_8$ alkanoyl" refers to an acyl group with 2 to 8 carbon atoms in a linear, branched or cycloalkyl arrangement, optionally substituted with 1 to 5 substituents independently selected at each occurrence from halogens, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, hydroxy, amino, mono or di($C_1$–$C_8$)alkyl amino, ($C_3$–$C_7$)cycloalkyl($C_0$–$C_3$)alkyl, halo($C_1$–$C_8$)alkyl, halo($C_1$–$C_8$)alkoxy, $C_1$–$C_8$ alkanoyl, $C_1$–$C_8$ alkoxycarbonyl, —COOH, —CONH$_2$, mono- or di-($C_1$–$C_8$)alkylcarboxamido, —SO$_2$NH$_2$, and mono or di($C_1$–$C_8$)alkylsulfonamido.

By "$C_1$–$C_8$ alkoxy," in the present invention, is meant an alkyl group of 1 to 8 carbon atoms attached via an oxygen bridge. $C_1$–$C_8$ alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy. $C_1$–$C_6$ alkoxy groups are generally preferred, with $C_1$–$C_4$ alkoxy groups particularly preferred, especially ethoxy and methoxy. Similarly, "$C_1$–$C_8$ alkylthio" refers to an alkyl group of 1 to 8 carbon atoms attached via a sulfur bridge.

The term "$C_1$–$C_8$ alkoxycarbonyl" refers to an alkoxy group linked via a carbonyl. In other words, an alkoxycarbonyl group has the general structure —C(=O)—O-alkyl. $C_1$–$C_6$ alkyl groups are generally preferred, with $C_1$–$C_4$ alkyl groups particularly preferred.

"$C_1$–$C_8$ alkanoyloxy," as used herein, refers to an alkanoyl group linked via an oxygen bridge. In other words, an alkanoyloxy group has the general structure —O—C(=O)-alkyl. $C_1$–$C_6$ alkyl groups are generally preferred, with $C_1$–$C_4$ alkyl groups particularly preferred.

The term "$C_1$–$C_8$ carbonate" refers to an alkoxycarbonyl group linked via an oxygen bridge. In other words, a carbonate group has the general structure —O—C(=O)—O-alkyl. $C_1$–$C_6$ alkyl groups are generally preferred, with $C_1$–$C_4$ alkyl groups particularly preferred.

"$C_2$–$C_8$ alkanone" refers to a ketone substituent with 2 to 8 carbon atoms in a linear, branched or cyclic arrangement, optionally substituted with 1 to 5 substituents independently selected at each occurrence from halogens, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, hydroxy, amino, mono or di($C_1$–$C_8$)alkyl amino, ($C_3$–$C_7$)cycloalkyl($C_0$–$C_3$)alkyl, halo($C_1$–$C_8$)alkyl, halo($C_1$–$C_8$)alkoxy, $C_1$–$C_8$ alkanoyl, $C_1$–$C_8$ alkoxycarbonyl, —COOH, —CONH$_2$, mono- or di-($C_1$–$C_8$)alkylcarboxamido, —SO$_2$NH$_2$, and mono or di($C_1$–$C_8$)alkylsulfonamido.

Similarly, "$C_2$–$C_8$ alkyl ether" refers to an ether substituent with 2 to 8 carbon atoms, optionally substituted with 1 to 5 substituents independently selected at each occurrence from halogens, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, hydroxy, amino, mono or di($C_1$–$C_8$)alkyl amino, ($C_3$–$C_7$)cycloalkyl($C_0$–$C_3$)alkyl, halo($C_1$–$C_8$)alkyl, halo($C_1$–$C_8$)alkoxy, $C_1$–$C_8$ alkanoyl, $C_1$–$C_8$ alkoxycarbonyl, —COOH, —CONH$_2$, mono- or di-($C_1$–$C_8$)alkylcarboxamido, —SO$_2$NH$_2$, and mono or di($C_1$–$C_8$)alkylsulfonamido. Such a substituent is attached via a carbon atom on either side of the ether linkage.

The term "halogen" includes fluorine, chlorine, bromine and iodine. A "haloalkyl" may be a branched or straight-chain saturated aliphatic hydrocarbon group, substituted with 1 or more halogen atoms. "Halo($C_1$–$C_8$)alkyl" groups have 1 to 8 carbon atoms; "halo($C_1$–$C_6$)alkyl" groups have 1 to 6 carbon atoms. Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Preferably not more than 5, and more preferably not more than 3, haloalkyl groups are present in compounds provided herein. The term "haloalkoxy" refers to a haloalkyl group as defined above attached via an oxygen bridge. "Halo(C$_1$–C$_8$)alkoxy" groups have 1 to 8 carbon atoms.

The term "hydroxy(C$_1$–C$_8$)alkyl" (or "hydroxy(C$_1$–C$_6$) alkyl") refers to aliphatic group having from 1 to 8 (or 1 to 6) carbon atoms, and further comprising at least one hydroxyl group on the main carbon chain and/or on a side chain. Hydroxy(C$_1$–C$_8$)alkyl groups include, for example, 2-hydroxy-1,1-dimethyl-ethyl, 1-hydroxymethyl-2-methyl-propyl and 2-hydroxy-propyl.

The term "C$_1$–C$_8$ carbamate," as used herein, refers to a group having the general structure —N—C(=O)—O-alkyl. C$_1$–C$_6$ alkyl groups are generally preferred, with C$_1$–C$_4$ alkyl groups particularly preferred.

A "heteroatom," as used herein, is oxygen, sulfur or nitrogen.

A "carbocyclic group" is ring formed entirely by carbon-carbon bonds. Unless otherwise specified, such a ring may be aromatic or non-aromatic. Representative examples of carbocyclic groups are cycloalkyl groups (e.g., cyclopentane and cyclohexane), as well as aromatic groups such as phenyl, benzyl, naphthyl, phenoxyl, benzoxyl and phenylethanonyl. Carbon atoms present within a carbocyclic group may, of course, be further bonded to a variety of ring substituents, such as hydrogen, a halogen, cyano, nitro, C$_1$–C$_8$ alkyl, C$_2$–C$_8$ alkenyl, C$_2$–C$_8$ alkynyl, C$_1$–C$_8$ alkoxy, C$_1$–C$_8$ alkylthio, hydroxy, amino, mono or di(C$_1$–C$_8$)alkyl amino, (C$_3$–C$_7$)cycloalkyl(C$_0$–C$_3$)alkyl, halo(C$_1$–C$_8$)alkyl, halo(C$_1$–C$_8$)alkoxy, C$_1$–C$_8$ alkanoyl, C$_1$–C$_8$ alkoxycarbonyl, —COOH, —CONH$_2$, mono- or di-(C$_1$–C$_8$)alkylcarboxamido, —SO$_2$NH$_2$, and mono or di(C$_1$–C$_8$)alkylsulfonamido.

A "heterocyclic group" comprises a ring in which at least one ring atom is a heteroatom (i.e., N, O or S), and the remainder of the ring atoms are carbon. Preferably, a heterocyclic group comprises 1–4 heteroatoms; within certain embodiments 1 or 2 heteroatoms is preferred. A heterocyclic group generally has from 1 to 3 fused or pendant rings, preferably one ring or two fused rings. Typically, each ring contains from 5 to 10 ring members, and may be optionally substituted with from 1 to 5 substituents such as halogen, cyano, nitro, C$_1$–C$_8$ alkyl, C$_2$–C$_8$ alkenyl, C$_2$–C$_8$ alkynyl, C$_1$–C$_8$ alkoxy, C$_1$–C$_8$ alkylthio, hydroxy, amino, mono or di(C$_1$–C$_8$)alkyl amino, halo(C$_1$–C$_8$)alkyl, halo(C$_1$–C$_8$) alkoxy, hydroxy(C$_1$–C$_8$)alkyl, hydroxy(C$_1$–C$_8$)alkoxy C$_2$–C$_8$ alkanoyl, C$_1$–C$_8$ alkoxycarbonyl, COOH, —SO$_2$NH$_2$, mono or dialkylsulfonamido, —C(O)NH$_2$ or mono or di(C$_1$–C$_8$)alkylcarboxamido. Unless otherwise specified, a heterocyclic group may be aromatic or nonaromatic. As with a carbocyclic group, atoms within a heterocyclic ring may be further linked to a variety of ring substituents.

Examples of heterocyclic groups include, but are not limited to, acridinyl, azocinyl, benzimidazolyl, benzofuranyl, benzothio-furanyl, benzothiophenyl, benzoxazolyl, benzothiazolyl, benzotriazolyl, benoztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, dithiazinyl, dihydrofurotetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, quinuclidinyl, tetrahydrofuranyl, tetrahydroisoquinolinyl, tetrahydroquinolinyl, thiadiazinyl, thiadiazolyl, thianthrenyl, thiazolyl, thienyl, thienothiazolyl, thienooxazolyl, thienoimidazolyl, thiophenyl, triazinyl and xanthenyl. It will be apparent that any such heterocyclic groups may be substituted with one or more substituents as described above.

Preferred heterocyclic groups include, for example, pyrimidinyl (e.g., pyrimidin-2-yl), pyridinyl (pyridin-2-yl, pyridin-3-yl and pyridin-4-yl), morpholinyl (e.g., morpholin-4-yl), piperidinyl (e.g., piperdin-1-yl), pyrrolidinyl (e.g., pyrrolidin-1-yl), tetrazolyl, triazinyl, imidazolyl, oxazolyl, isoxazolyl, indolyl, pyrrolyl, pyrazolyl, quinolinyl, isoquinolinyl, thiazolyl, benzothiadiazolyl, triazolyl, pyrazinyl, furanyl, thienyl, benzothienyl, benzofuranyl, tetrahydropyranyl, indanyl, and substituted derivatives of the foregoing such as methyl-tetrahydropyran-2-yl and 2-hydroxy-indan-1-yl.

A "substituent," as used herein, refers to a molecular moiety that is covalently bonded to an atom within a molecule of interest. For example, a "ring substituent" may be a moiety such as a halogen, alkyl group, haloalkyl group or other group as discussed herein, that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

The term "NPY receptor" refers to a protein comprising any NPY receptor polypeptide sequence, with mammalian and especially human and monkey sequences generally preferred. "NPY5 receptor" refers to a protein comprising a NPY receptor subtype Y$_5$ sequence, such as those described within U.S. Pat. No. 5,602,024 and herein. An NPY or NPY5 receptor may consist entirely of a naturally-occurring sequence, or may comprise additional components (e.g., N-terminal leader sequence) that do not substantially inhibit the receptor's ability to bind ligand (i.e., at least 50% of the binding affinity of the receptor for NPY and/or PYY is retained). For example, a chimeric NPY5/NPY1 receptor, as described herein, is considered to be an NPY5 receptor. Similarly, truncated NPY receptor sequences, or sequences containing amino acid deletions, substitutes, additions or modifications may be used, provided that NPY receptor binding properties are not substantially diminished (i.e., at least 50% of the endogenous ligand-binding affinity is retained). The binding affinity of a candidate NPY receptor for ligand may be evaluated using a standard binding assay as provided herein (see also J. Clin. Invest. (1998) 102: 2136).

A "NPY5 receptor modulator," also referred to herein as a "modulator," is a compound that modulates (i.e., increases or decreases) ligand binding to NPY5 receptor. In other words, a modulator may be an NPY5 receptor antagonist or agonist. Modulators comprise a compound that is a 2-cyclohexyl-4-phenyl-1H-imidazole derivative having NPY5 receptor modulating activity. A modulator may consist entirely of such a compound, or may further comprise one or more additional moieties, provided that the modulating activity of the active compound is not substantially diminished (i.e., the ability to increase or decrease ligand binding to NPY5 receptor, as determined using a binding assay provided herein, is not diminished by more than 50%). Such additional moieties include, for example, targeting moieties, other active agents and carriers, any of which may be linked to the active compound via a variety of standard techniques including direct condensation, or by way of bi- or multi-functional linkers.

Alternatively, such additional moieties may be combined with the active compound, without covalent linking. A modulator binds "specifically" to NPY5 receptor if it binds human NPY5 receptor (total binding minus nonspecific binding) with a Ki that is 10-fold, preferably 100-fold, and more preferably 1000-fold, less than the Ki measured for modulator binding to other NPY receptors, such as NPY1. A modulator binds with "high affinity" if the $K_i$ at an NPY receptor is less than 1 micromolar, preferably less than 100 nanomolar or 10 nanomolar. Binding assays for evaluating Ki may be performed, for example, using the human in vitro NPY5 binding assay provided herein. Ligand binding to NPY1 receptor may be inhibited within such assays using well known techniques, such as through the use of Thomae compound, as described herein. It will be apparent that either NPY or PYY may be used as the ligand within binding assays.

A "targeting moiety," as used herein is a substance (e.g., a compound or a cell) that increases the local concentration of a modulator in the vicinity of a target site in a patient. There are a wide variety of targeting moieties known in the art, including antibodies and fragments thereof, receptors, ligands and other molecules that bind to cells of, or close to, a target tissue.

A "carrier," "carrier group" or "carrier molecule" is a substance that may be associated with an active compound prior to administration to a patient, generally for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding either directly or via a linker group, noncovalent interaction or admixture.

A moiety is "associated with" an active compound if the moiety is linked to (covalently or noncovalently) or combined with the active compound.

A "linker," as used herein, is any molecule that does not comprise a compound that modulates NPY binding to an NPY5 receptor, and that can be covalently linked to at least two chemical moieties. Linkers may be used to link another moiety to a compound that modulates NPY binding to an NPY5 receptor. In general, a linker is bi-functional or multi-functional (e.g., a branched structure). Numerous linkers are known in the art, and may be incorporated into an NPY receptor modulator using any appropriate method, which will be apparent to those of ordinary skill in the art.

A "prodrug" is a compound that does not fully satisfy the structural requirements of the compounds provided herein, but is modified in vivo, following administration to a patient, to produce an active compound of the present invention. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein.

A "patient" is any individual treated with a NPY5 receptor modulator as provided herein. Patients include humans, as well as other animals such as companion animals and livestock. Patients may be afflicted with a condition associated with undesirable NPY5 receptor activation, or may be free of such a condition (i.e., treatment may be prophylactic).

NPY5 Receptor Modulators

As noted above, the present invention provides neuropeptide $Y_5$ (NPY5) receptor modulators (i.e., agents that detectably modulate both ligand binding to NPY5 and NPY5 receptor-mediated signal transduction). Such modulators may be specific for NPY5 (i.e., do not detectably modulate ligand binding to other NPY receptors), or may also inhibit or enhance ligand binding to one or more additional NPY receptors, such as NPY1. NPY5 receptor modulators may be used to modulate NPY binding to NPY5 in vivo, especially in the treatment of feeding disorders (e.g., obesity and bulemia), psychiatric disorders, diabetes and cardiovascular diseases in humans, domesticated companion animals and livestock animals. Modulators may also be used within a variety of in vitro assays, such as assays for receptor activity, as probes for detection and localization of NPY5 receptors and as standards in assays of NPY binding and NPY-mediated cellular functions.

The NPY5 receptor modulators provided herein comprise active compounds that are substituted derivatives of 2-cyclohexyl-4-phenyl-1H-imidazole, which detectably modulate the binding of NPY to NPY5 receptor at nanomolar concentrations, preferably at subnanomolar concentrations. Certain active compounds bind specifically and/or with high affinity to NPY5 receptor. Active compounds may include receptor agonists and antagonists.

The present invention is based, in part, on the discovery that small molecules having the general formula I (as well as pharmaceutically acceptable salts and prodrugs thereof) modulate NPY binding to NPY5 receptor. Within the context of the present invention, it has been found that the cyclohexyl group in Formula I provides enhanced activity, compared to a heterocyclic ring.

Formula I

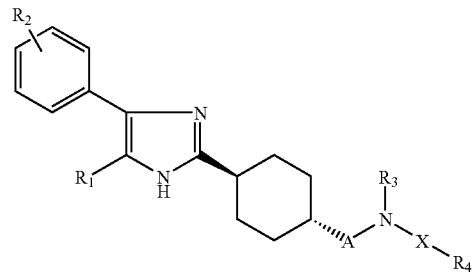

Within Formula 1, $R_1$ represents, within certain embodiments, a nonaromatic group such as hydrogen, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, halo($C_1$–$C_8$)alkyl, halo($C_1$–$C_8$)alkoxy, hydroxy($C_1$–$C_8$)alkyl, hydroxy($C_1$–$C_8$)alkoxy, mono or di($C_1$–$C_8$)

alkyl amino, $C_1$–$C_8$ alkanoyl, $C_1$–$C_8$ alkoxycarbonyl, $C_1$–$C_8$ alkanoyloxy, $C_1$–$C_8$ carbonate, $C_1$–$C_8$ carbamate, —COOH, —$SO_2NH_2$, mono or dialkylsulfonamido, —C(O)$NH_2$ or mono or di($C_1$–$C_8$)alkylcarboxamido. Alternatively, within other embodiments, $R_1$ is taken together with $R_2$, to form a carbocyclic or heterocyclic ring that is fused to the phenyl and imidazole rings of Formula I. The phrase "$R_1$ taken together with $R_2$," as used herein, is intended to refer to a covalent attachment between $R_1$ and $R_2$. It will be apparent to those of ordinary skill in the art that a ring formed by such an attachment also includes two carbon atoms that are members of the phenyl group, and two carbon atoms that are members of the imidazole ring of Formula I. One such representative structure is shown in Formula III. A ring generated by $R_1$ taken together with $R_2$ typically has from 5 to 7 ring members. Preferred $R_1$ groups include hydrogen, $C_1$–$C_6$ alkyl and groups that, when taken together with $R_2$, form a six-membered ring.

Formula III

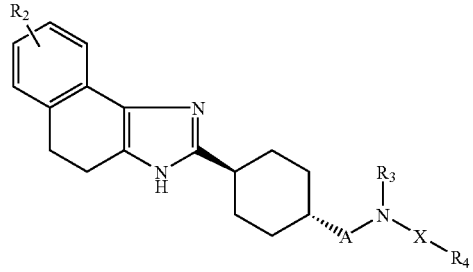

$R_2$, within Formula I, represents 0 to 5 ring substituents (i.e., 0 or 1 substituent at each carbon atom of the benzene ring), preferably 0 to 3 substituents, and more preferably 0 or 1 substituent. Each optional, independently selected substituent may be a nonaromatic group such as hydrogen, halogen, hydroxyl, amino, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_1$–$C_8$ carbonate, $C_1$–$C_8$ carbamate, $C_1$–$C_8$ alkylthio, halo($C_1$–$C_8$)alkyl, halo($C_1$–$C_8$)alkoxy, hydroxy($C_1$–$C_8$)alkyl, hydroxy($C_1$–$C_8$)alkoxy, mono or di($C_1$–$C_8$)alkyl amino, $C_1$–$C_8$ alkanoyl, $C_1$–$C_8$ alkoxycarbonyl, —COOH, —$SO_2NH_2$, mono and dialkylsulfonamido, —C(O)$NH_2$, mono and di($C_1$–$C_8$)alkylcarboxamido. Alternatively, an $R_2$ substituent may be taken together with $R_1$ to form a carbocyclic or heterocyclic ring that is fused to the phenyl and imidazole rings of Formula I, such as that shown in Formula II. As noted above, a ring so generated typically has from 5 to 7 ring members. Preferred $R_2$ groups include meta-substituted trifluoromethyl, halogen or cyano groups, as well as groups that, when taken together with $R_1$, form a six-membered ring. It will be apparent to those of ordinary skill in the art that one $R_2$ group may form a fused ring with $R_1$, while one or more other $R_2$ groups may be located elsewhere on the phenyl ring. It will be further apparent that combinations of $R_2$ substituents are permissible only if such combinations result in stable compounds. A stable compound or stable structure is meant to imply a compound that is sufficiently robust to survive isolation, characterization and testing for biological activity.

A, in Formula I, represents —C(O)— or —($CH_2$)$_n$—, wherein n is an integer ranging from 1 to 3, and preferably is —C(O)— or —$CH_2$—.

$R_3$, within certain embodiments, represents hydrogen or $C_1$–$C_8$ alkyl. Such an alkyl group may, but need not, be substituted with from 1 to 8 substituents that are independently selected from halogen, hydroxyl, carbocyclic groups and heterocyclic groups, wherein each carbocyclic or heterocyclic group contains from 3 to 10 ring members. Within other embodiments, $R_3$ is a bond to $R_4$, forming a heterocyclic group that comprises $R_3$, the nitrogen, X and $R_4$. Such a heterocyclic group generally contains from 1 to 3 fused or pendant rings, preferably a single ring or two fused rings, and each ring generally contains from 5 to 10 ring members. Each ring within such a heterocyclic group is optionally substituted with from 1 to 5 substituents that are independently selected from halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_1$–$C_8$ carbonate, $C_1$–$C_8$ carbamate, $C_1$–$C_8$ alkylthio, hydroxy, amino, mono or di($C_1$–$C_8$)alkyl amino, halo($C_1$–$C_8$)alkyl, halo($C_1$–$C_8$)alkoxy, hydroxy($C_1$–$C_8$)alkyl, hydroxy($C_1$–$C_8$)alkoxy $C_1$–$C_8$ alkanoyl, $C_1$–$C_8$ alkoxycarbonyl, COOH, —$SO_2NH_2$, mono or dialkylsulfonamido, —C(O)$NH_2$ and mono and di($C_1$–$C_8$)alkylcarboxamido. $R_3$ is preferably hydrogen, methyl, ethyl or propyl.

X, within Formula I, represents a bond, —S(O)$_2$—, —C(O)— or —NHC(O)—. If X is a bond, then the nitrogen is directly (covalently) bonded to $R_4$.

$R_4$ represents, within certain embodiments, represents hydrogen, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_1$–$C_8$ carbonate, halo($C_1$–$C_8$)alkyl, halo($C_1$–$C_8$)alkoxy, hydroxy($C_1$–$C_8$)alkyl hydroxy($C_1$–$C_8$)alkoxy, $C_1$-$C8_6$ alkanone or $C_1$–$C_8$ alkyl ether. Any such group (except hydrogen) is optionally substituted with from 1 to 8 substituents that are independently selected from halogen, hydroxyl, carbocyclic groups and heterocyclic groups. Any such carbocyclic or heterocyclic group contains from 5 to 10 ring members, preferably 5 to 7 ring members. Within other embodiments, $R_4$ represents a carbocyclic or heterocyclic group that contains from 1 to 3 fused or pendant rings, preferably a single ring or two fused rings, and each ring generally contains from 5 to 10 ring members. Each ring within such a carbocyclic or heterocyclic group is optionally substituted with from 1 to 5 substituents that are independently selected from halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_1$–$C_8$ carbonate, $C_1$–$C_8$ carbamate, $C_1$–$C_8$ alkylthio, hydroxy, amino, mono or di($C_1$–$C_8$)alkyl amino, halo($C_1$–$C_8$)alkyl, halo($C_1$–$C_8$) alkoxy, hydroxy($C_1$–$C_8$)alkyl, hydroxy($C_1$–$C_8$)alkoxy $C_1$–$C_8$ alkanoyl, $C_1$–$C_8$ alkoxycarbonyl, COOH, —$SO_2NH_2$, mono or dialkylsulfonamido, —C(O)$NH_2$ and mono or di($C_1$–$C_8$)alkylcarboxamido. Within still further embodiments, $R_4$ is taken together with $R_3$ and X to form a heterocyclic group that comprises $R_3$, the nitrogen, X and $R_4$. The phrase "taken together with $R_3$ and X" is intended to refer to embodiments in which $R_4$ is covalently bonded to $R_3$, forming at least one ring that comprises $R_3$, the nitrogen, X and $R_4$. The entire heterocyclic group generally contains from 1 to 3 fused or pendant rings, preferably a single ring or two fused rings, and each ring generally contains from 5 to 10 ring members. Each ring within such a heterocyclic group may, but need not, be substituted by from 1 to 5 substituents that are independently selected from halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_1$–$C_8$ carbonate, $C_1$–$C_8$ carbamate, $C_1$–$C_8$ alkylthio, hydroxy, amino, mono or di($C_1$–$C_8$)alkyl amino, halo($C_1$–$C_8$)alkyl, halo($C_1$–$C_8$) alkoxy, hydroxy($C_1$–$C_8$)alkyl, hydroxy($C_1$–$C_8$)alkoxy $C_1$–$C_8$ alkanoyl, $C_1$–$C_8$ alkoxycarbonyl, —COOH, —SO$_2$NH$_2$, mono or dialkylsulfonamido, —C(O)NH$_2$ and mono or di($C_1$–$C_8$)alkylcarboxamido.

Preferred R$_4$ groups include aromatic groups such as phenyl, benzyl, phenoxyl, benzoxyl, phenylethanonyl, pyrimidin-2-yl, pyrimidin-4-yl, pyrimidin-5-yl, tetrahydropyran-2-yl, 2-hydroxy-indan-1-yl, tetrazolyl, pyrimidin-2-yl, pyridin-2-yl, pyridin-3-yl and pyridin-4-yl. Any such groups may, but need not, be substituted by from 1 to 3 substituents independently selected from hydroxyl, halogen and $C_1$–$C_6$ alkyl. Other preferred R$_4$ groups are the non-aromatic groups hydrogen, $C_1$–$C_6$ alkyl, $C_1$–$C_6$ alkoxyl, halo($C_1$–$C_6$)alkyl, halo($C_1$–$C_6$)alkoxyl, hydroxy($C_1$–$C_6$)alkyl, hydroxy($C_1$–$C_6$)alkoxyl, $C_1$–$C_6$ alkanone and $C_1$–$C_6$ alkyl ether. Still further preferred R$_4$ groups are those in which R$_4$ is taken with X, R$_3$ and the N bonded to R$_3$ to form a heterocyclic group such as tetrazolyl, morpholin-4-yl, pyrimidin-2-yl, pyridin-2-yl, pyridin-3-yl and pyridin-4-yl, piperdin-1-yl, pyrrolidin-1-yl and derivatives of the foregoing in which from 1 to 3 ring members are substituted with a substituent independently selected from halogen, $C_1$–$C_6$ alkyl, $C_1$–$C_6$ alkoxyl, hydroxyl, halo($C_1$–$C_6$)alkyl and halo($C_1$–$C_6$)alkoxyl.

Certain representative compounds provided herein satisfy one of the following criteria:

(i) X is S)$_2$, R$_3$ is hydrogen and R$_4$ is a group selected from phenyl, pyridyl and pyrimidyl, wherein the group is optionally substituted by from 1 to 3 substituents independently selected from hydroxyl, halogen and $C_1$–$C_6$ alkyl;

(ii) A is —CH$_2$—, X is —C(O)—, R$_3$ is hydrogen and R$_4$ is $C_1$–$C_6$ alkyl, $C_1$–$C_6$ alkoxyl, halo($C_1$–$C_6$)alkyl or halo($C_1$–$C_6$)alkoxyl;

(iii) A is —C(O)—, X is NHC(O)—, R$_3$ is hydrogen and R$_4$ is $C_1$–$C_6$ alkyl; or (iv) A is —C(O)—, X is a bond, R$_3$ is hydrogen or $C_1$–$C_6$ alkyl, and R$_4$ is $C_1$–$C_6$ alkyl, halo($C_1$–$C_6$)alkyl, hydroxy($C_1$–$C_6$)alkyl, or an aromatic group selected from phenyl, pyrimidin-2-yl, indan-1-yl, wherein the group is optionally substituted by from 1 to 3 substituents independently selected from hydroxyl, halogen, $C_1$–$C_6$ alkyl, hydroxy($C_1$–$C_6$)alkyl and $C_1$–$C_6$ alkanone.

Representative compounds provided herein include, but are not limited to, (a) 2-Chloro-N-{4-[4-(3-trifluoromethyl-phenyl)-1H-imidazol-2-yl]-cyclohexanecarbonyl}-benzene sulfonamide; (b) 4-[4-(3-Trifluoromethyl-phenyl)-1H-imidazol-2-yl]-cyclohexanecarboxylic acid(2-hydroxy-propyl)-methyl-amide; (c) 4-[4-( 3-Trifluoromethyl-phenyl)-1H-imidazol-2-yl]-cyclohexane carboxylic acid(2-oxo-2-phenyl-ethyl)-amide; (d) Pyridine-3-sulfonic acid{4-[4-(3-trifluoro-methyl-phenyl)-1H-imidazol-2-yl]-cyclohexylmethyl}-amide; (e) 4-[4-(3-Trifluoromethyl-phenyl)-1H-imidazol-2-yl]-cyclohexanecarboxylic acid(2-hydroxy-2-phenyl-ethyl)-amide; (f) 1-{4-[4-(3-Trifluoromethyl-phenyl)-1H-imidazol-2-yl]-cyclohexylmethyl}-1H-tetrazole; (g) N-{4-[4-(3-Trifluoromethyl-phenyl)-1H-imidazol-2-yl]-cyclohexylmethyl}-benzenesulfonamide; (h) 4-[4-(3-Trifluoromethyl-phenyl)-1H-imidazol-2-yl]-cyclohexanecarboxylic acid(2-hydroxy-indan-1-yl)-amide; (i){4-[4-(3-Chloro-phenyl)-1H-imidazol-2-yl]-cyclohexyl-methyl}-carbamic acid ethyl ester; (j) Cyclopentyl-{4-[4-(3-trifluoromethyl-phenyl)-1H-imidazol-2-yl]-cyclohexylmethyl}-amine; (k) N-{4-[4-(4-Bromo-phenyl)-1H-imidazol-2-yl]-cyclohexyl-methyl}-2,2,2-trifluoro-acetamide; (l) N-{4-[4-(3-trifluoromethyl-phenyl)-1H-imidazol-2-yl]-cyclohexanecarbonyl}-benzene sulfonamide; (m) Pyrimidin-2-yl-{4-[4-(3-trifluoromethyl-phenyl)-1H-imidazol-2-yl]-cyclohexylmethyl}-amine; (n) 4-[4-(3-Bromo-phenyl)-1H-imidazol-2-yl]-cyclohexanecarboxylic acid N-acetyl-hydrazide; (o) 4,N-Dimethyl-N-{4-[4-(3-trifluoromethyl-phenyl)-1H-imidazol-2-yl]-cyclohexanecarbonyl}-benzene sulfonamide; (p) N-{4-[4-(3-Trifluoromethyl-phenyl)-1H-imidazol-2-yl]-cyclohexylmethyl}-acetamide; (q) Benzenesulfinic acid {4-[4-(3-chloro-phenyl)-1H-imidazol-2-yl]-cyclohexylmethyl}-amide; (r) 4-[4-(3-Trifluoromethyl-phenyl)-1H-imidazol-2-yl]-cyclohexanecarboxylic acid(2-hydroxy-1,1-dimethyl-ethyl)-amide; (s) 4-Hydroxy-N-{4-[4-(3-trifluoromethyl-phenyl)-1H-imidazol-2-yl]-cyclohexylmethyl}-butyramide; (t) 4-methyl-N-{4-[4-(3-trifluoromethyl-phenyl)-1H-imidazol-2-yl]-cyclohexanecarbonyl}-benzene sulfonamide; (u) N-{4-[4-(3-Bromo-phenyl)-1H-imidazol-2-yl]-cyclohexylmethyl}-trifluoroacetamide; (v) 4-[4-(3-Trifluoromethyl-phenyl)-1H-imidazol-2-yl]-cyclohexanecarboxylic acid (2-hydroxy-propyl)-amide; (w) N-{4-[5-methyl-4-(3-trifluoromethyl-phenyl)-1H-imidazol-2-yl]-cyclohexylmethyl}-acetamide; (x) 2,2,2-Trifluoro-N-{4-[4-(4-methoxy-phenyl)-1H-imidazol-2-yl]-cyclohexylmethyl}-acetamide; (y) 4-Chloro-N-{4-[4-(3-trifluoromethyl-phenyl)-1H-imidazol-2-yl]-cyclohexanecarbonyl}-benzene sulfonamide; (z) N-[4-(8-Methoxy-4,5-dihydro-3H-naphtho[1,2-d]imidazol-2-yl)-cyclohexylmethyl]-benzenesulfonamide; (aa) 4-[4-(3-Bromo-phenyl)-1H-imidazol-2-yl]-cyclohexanecarboxylic acid pyrimidin-2-ylamide; (bb) N-Methyl-N-{4-[4-(3-trifluoromethyl-phenyl)-1H-imidazol-2-yl]-cyclohexylmethyl}-benzenesulfonamide; (cc) N-{4-[4-(3-Bromo-phenyl)-1H-imidazol- 2-yl]-cyclohexylmethyl}-acetamide; (dd) 5-Methyl-pyridine-2-sulfonic acid{4-[4-(3-trifluoromethyl-phenyl)-1H-imidazol-2-yl]-cyclohexanecarbonyl}-amide; (ee) 4-[4-(3-Trifluoromethyl-phenyl)-1H-imidazol-2-yl]-cyclohexanecarboxylic acid (1-hydroxymethyl-2-methyl-propyl)-amide; (ff) {4-[5-Methyl-4-(3-trifluoromethyl-phenyl)-1H-imidazol-2-yl]-cyclohexylmethyl}-carbamic acid benzyl ester; (gg) [4-(8-Methoxy-4,5-dihydro-3H-naphtho [1,2-d]imidazol-2-yl)-cyclohexylmethyl]-carbamic acid benzyl ester; (hh) 4-[4-(3-Trifluoromethyl-phenyl)-1H-imidazol-2-yl]-cyclohexanecarboxylic acid N-acetyl-hydrazide; (ii) 2,2,2-Trifluoro-N-[4-(4-phenyl-1H-imidazol-2-yl]-cyclohexylmethyl]-acetamide; and (jj) 2,2,2-Trifluoro-N-{4-[4-(3-trifluoromethyl-phenyl)-1H-imidazol-2-yl]-cyclohexylmethyl}-acetamide.

Certain representative compounds encompassed by Formula I are illustrated in Table I. Within Table I, reference is made to Formula IV, and the following abbreviations are used: Ph is phenyl, Me is methyl, Et is ethyl, nPr or Pr is n-propyl, iPr is isopropyl, tBu is tert-butyl, cPent is cyclopentyl, cHex is cyclohexyl.

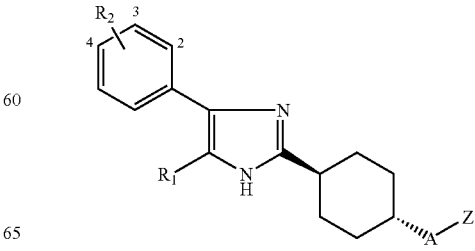

Formula IV

TABLE I

| Compound | A | R₁ | R₂ | Z |
|---|---|---|---|---|
| 1 | $CH_2$ | H | 3-Cl | NH—$SO_2$Ph |
| 2 | $CH_2$ | H | 3-Cl | NH—$CO_2CH_2$Ph |
| 3 | $CH_2$ | H | 3-Cl | NH—$CO_2CH_2CH_3$ |
| 4 | $CH_2$ | H | H | NH—$SO_2CH_3$ |
| 5 | $CH_2$ | H | 3-$CF_3$ | —$NH_2$ |
| 6 | $CH_2$ | H | 3-$CF_3$ | NH—$SO_2$Ph |
| 7 | $CH_2$ | H | 3-$CF_3$ | $N(CH_3)$—$SO_2$Ph |
| 8 | $CH_2$ | H | 3-$CF_3$ | NHC=O($CH_3$) |
| 9 | $CH_2$ | H | 3-$CF_3$ | $NHCH_2CH_3$ |
| 10 | $CH_2$ | H | 3-$CF_3$ | NH-cyclopentyl |
| 11 | $CH_2$ | H | 3-$CF_3$ | N—$(CH_2CH_2CH_3)_2$ |
| 12 | $CH_2$ | H | 3-Br | NHC=O($CF_3$) |
| 13 | $CH_2$ | H | 3-Br | NHC=O($CH_3$) |
| 14 | $CH_2$ | H | CN | NHC=O($CH_3$) |
| 15 | $CH_2$ | H | 3-$CF_3$ | NH-tetrahydropyran-4-yl |
| 16 | $CH_2$ | H | 3-$CF_3$ | NHC=O$(CH_2)_3$OH |
| 17 | $CH_2$ | H | 3-$CF_3$ | NHC=O$CH_2CH(OH)CH_3$ |
| 18 | $CH_2$ | $CH_3$ | 3-$CF_3$ | NH—$CO_2CH_2$Ph |
| 19 | $CH_2$ | $CH_3$ | 3-$CF_3$ | NH-cyclopentyl |
| 20 | $CH_2$ | $CH_3$ | 3-$CF_3$ | NHC=O($CH_3$) |
| 21 | $CH_2$ | H | H | NHC=O($CF_3$) |
| 22 | $CH_2$ | H | 4-$OCH_3$ | NHC=O($CF_3$) |
| 23 | $CH_2$ | H | 3-$CF_3$ | NHC=O($CF_3$) |
| 24 | $CH_2$ | H | H | NHC=O($CH_3$) |
| 25 | $CH_2$ | H | 4-Br | NHC=O($CF_3$) |
| 26 | $CH_2$ | H | 4-Br | NHC=O($CH_3$) |
| 27 | $CH_2$ | H | 3-$CF_3$ | NH-pyrimidin-2-yl |
| 28 | $CH_2$ | H | H | NH—$CH_2CF_3$ |
| 29 | $CH_2$ | H | 4-Br | —$NH_2$ |
| 30 | $CH_2$ | H | 4-Br | $NHCH_2$(tetrahydropyran-2-yl) |
| 31 | $CH_2$ | H | 4-Br | morpholin-4-yl |
| 32 | $CH_2$ | H | 3-$CF_3$ | NH—$SO_2$-(pyridin-3-yl) |
| 33 | $CH_2$ | H | H | NHC=O (pyridin-3-yl) |
| 34 | $CH_2$ | H | H | NH—$SO_2$-(pyridin-3-yl) |
| 35 | $CH_2$ | H | 3-Cl | NHC=O(pyridin-3-yl) |
| 36 | $CH_2$ | H | 3-Cl | NH—$SO_2$-(pyridin-3-yl) |
| 37 | C=O | H | 3-$CF_3$ | NHNHC=O($CH_3$) |
| 38 | C=O | H | 3-$CF_3$ | $NHSO_2$-(4-$CH_3$-phenyl) |
| 39 | C=O | H | 3-Br | NHNHC=O($CH_3$) |
| 40 | C=O | H | 3-Br | $NH(CH_2)_2CH_3$ |
| 41 | C=O | H | 3-Br | NH-pyrimidin-2-yl |
| 42 | C=O | H | 3-Br | N-$(CH_2CH_2CH_3)_2$ |
| 43 | C=O | H | 3-Br | $NHCH_2CH(OH)CH_3$ |
| 44 | C=O | H | 3-Br | $NHCH_2C$=O($CH_3$) |
| 45 | C=O | H | 3-$CF_3$ | $NHSO_2$-(2-Cl-phenyl) |
| 46 | C=O | H | 3-$CF_3$ | $NHSO_2$-(3-Cl-phenyl) |
| 47 | C=O | H | 3-$CF_3$ | $NHSO_2$-(4-Cl-phenyl) |
| 48 | C=O | H | 3-$CF_3$ | $NHSO_2$-Ph |
| 49 | C=O | H | 3-$CF_3$ | $NHSO_2$(5-$CH_3$-pyridin-2-yl) |
| 50 | C=O | H | 3-$CF_3$ | $NHSO_2CH_2$Ph |
| 51 | C=O | H | 3-$CF_3$ | $NHSO_2$-(2-$CH_3$-phenyl) |
| 52 | C=O | H | 3-$CF_3$ | (R)-$NHCH_2CH(OH)CH_3$ |
| 53 | C=O | H | 3-$CF_3$ | (S)-$NHCH_2CH(OH)CH_3$ |
| 54 | C=O | H | 3-$CF_3$ | NH—$SO2(CH_2)_3CH_3$ |
| 55 | C=O | H | 3-$CF_3$ | NH—$SO2(CH_2)_2CH_3$ |
| 56 | C=O | H | 3-$CF_3$ | NH—$SO2CH_2CH_3$ |
| 57 | C=O | H | 3-$CF_3$ | NH—$SO2CH_2CF_3$ |
| 58 | C=O | H | 3-$CF_3$ | $NCH_3$—$SO_2$-(4-$CH_3$-phenyl) |
| 59 | C=O | H | 3-$CF_3$ | $NH(CH_2)_2OH$ |
| 60 | C=O | H | 3-$CF_3$ | $NHC(CH_3)_2CH_2OH$ |
| 61 | C=O | H | 3-$CF_3$ | $NHCH(CH_3)CH_2OH$ |
| 62 | C=O | H | 3-$CF_3$ | $NH(CH_2)_3OH$ |
| 63 | C=O | H | 3-$CF_3$ | $NHCH_2CH(OH)Ph$ |
| 64 | C=O | H | 3-$CF_3$ | $NH(CH2)_2CH(OH)CH_3$ |
| 65 | C=O | H | 3-$CF_3$ | $NHCH(CH_2OH)CH(CH_3)_2$ |
| 66 | C=O | H | 3-$CF_3$ | $NHCH_2CH(OH)CH_2CH_3$ |
| 67 | C=O | H | 3-$CF_3$ | NH-1-$(CH_2OH)$cyclopent-1-yl |
| 68 | C=O | H | 3-$CF_3$ | NH(1-OH-cyclohexyl)-methyl |
| 69 | C=O | H | 3-$CF_3$ | NH-(2-OH-cyclohex-1-yl) |
| 70 | C=O | H | 3-$CF_3$ | $NH(CH_2)_2OCH_3$ |
| 71 | C=O | H | 3-$CF_3$ | $NH(CH_2)_2NH_2$ |
| 72 | C=O | H | 3-$CF_3$ | $NH(CH_2)_2N(CH_3)_2$ |
| 73 | C=O | H | 3-$CF_3$ | morpholin-4-yl |
| 74 | C=0 | H | 3-$CF_3$ | NH-cyclohexyl |
| 75 | C=O | H | 3-$CF_3$ | $NCH_3$—$CH_2CH(OH)CH_3$ |
| 76 | C=O | H | 3-$CF_3$ | (S)-$NHCH_2CH(OH)Ph$ |
| 77 | C=O | H | 3-$CF_3$ | (R)-$NHCH_2CH(OH)Ph$ |
| 78 | C=O | H | 3-$CF_3$ | 3-(OH)-piperidin-1-yl |
| 79 | C=O | H | 3-$CF_3$ | 3-(OH)-pyrrolidin-1-yl |
| 80 | C=O | H | 3-$CF_3$ | (1R, 2S)NH(2-OH-indan-1-yl) |
| 81 | C=O | H | 3-$CF_3$ | (1S, 2R)NH(2-OH-indan-1-yl) |
| 82 | C=O | H | 3-$CF_3$ | 4-(OH)-piperidin-1-yl |
| 83 | C=O | H | 3-$CF_3$ | NH—$CH_2CH(OH)C(CH_3)_3$ |
| 84 | C=O | H | 3-$CF_3$ | (S)—NH—$CH(CH_2OH)CH(CH_3)_2$ |
| 85 | C=O | H | 3-$CF_3$ | (R)—NH—$CH(CH_2OH)CH(CH_3)_2$ |
| 86 | C=O | H | 3-$CF_3$ | NH—$CH_2CH(OH)CF_3$ |

It will be apparent to those of ordinary skill in the art that Table I provides only representative examples of compounds provided herein, and is not intended to limit the scope of the present invention. Further, as noted above, all compounds of the present invention may be present as a free base or as a pharmaceutically acceptable acid addition salt.

Substituted derivatives of 2-cyclohexyl-4-phenyl-1H-imidazole provided herein detectably alter (modulate) NPY binding to NPY5 receptor, as determined using standard in vitro NPY5 receptor ligand binding assays and/or signal transduction assays. References herein to an "NPY5 receptor ligand binding assay" are intended to refer to the protocol provided in Example 11. Briefly, a competition assay may be performed in which an NPY5 receptor preparation is incubated with labeled (e.g., $^{125}$I) NPY and unlabeled test compound. Within the assays provided herein, the NPY5 receptor used is preferably a mammalian NPY5 receptor, more preferably a human or monkey NPY5 receptor. The receptor may be recombinantly expressed or naturally expressed, and may comprise a native sequence or a modified sequence (e.g., truncated and/or fused to a non-native N-terminal sequence). The NPY5 receptor preparation may be, for example, a membrane preparation from Sf9 cells or Bowes Melanoma cells that recombinantly express human NPY5 receptor or a human chimeric NPY5/NPY1 receptor.

Incubation with a compound that detectably modulates NPY binding to NPY5 receptor will result in a decrease or increase in the amount of label bound to the NPY5 receptor preparation, relative to the amount of label bound in the absence of the compound. Preferably, such a compound will exhibit a $K_i$ at an NPY5 receptor of less than 1 micromolar, more preferably less than 500 nM, 100 nM, 20 nM or 10 nM, within an assay performed as described in Example 11. Generally preferred compounds are NPY5 receptor antagonists, and decrease NPY5 receptor activity (as measured by calcium mobilization, as described in Example 12) by at least 20%, preferably by at least 50%, and most preferably by at least 80%. For certain uses, preferred compounds also decrease food intake and weight gain in one or more animal models, such as food deprivation models (as described, for example, in published PCT application PCT/US00/26887) and the bovine pancreatic polypeptide antagonism model, as described in Example 13.

If desired, compounds provided herein may be evaluated for certain pharmacological properties including, but not limited to, oral bioavailability, serum protein binding and in vitro and in vivo half-life. In addition, penetration of the blood brain barrier may be desirable for compounds used to treat CNS disorders, while low brain levels of compounds used to treat peripheral disorders may be preferred. Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound intravenously. Serum protein binding may be predicted from albumin binding assays, as described, for example, in a review by Oravcová et al. (Journal of Chromatography B (1996) 677:1–27). Compound half-life is inversely proportional to the frequency of dosage of a compound. In vitro half-lives of compounds may be predicted from assays of microsomal half-life as described by Kuhnz and Gieschen (Drug Metabolism and Disposition (1998)26:1120–1127). In view of the present disclosure, a person of ordinary skill in the art could use such routine techniques to select a compound that displays optimal properties for a particular purpose.

As noted above, NPY5 receptor modulators provided herein may comprise, in addition to an active compound of formula I, one or more additional associated moieties. Such moieties may be linked directly (i.e., via a bond) or by way of a linker, may be noncovalently linked or may be combined with the compound. Such additional moieties may be used, for example, to facilitate delivery, targeting or detection of the compound. For example, compounds provided herein may sufficiently target a desired site in vivo; however, it may be beneficial for certain applications to include an additional targeting moiety to facilitate targeting to one or more specific tissues. Preferred targeting moieties include those that target to brain regions associated with NPY5 activity.

For certain embodiments, it may be beneficial to also, or alternatively, associate a drug with a modulator. As used herein, the term "drug" refers to any bioactive agent intended for administration to a mammal to prevent or treat a disease or other undesirable condition. Drugs include hormones, growth factors, proteins, peptides and other compounds. For example, modulators for treatment of eating disorders, particularly obesity and bulimia nervosa, may comprise an agent such as sibutramine, dexenfluramine, leptin, a growth hormone secretagogue, a melanocortin agonist, a beta- 3 agonist, a 5HT-2 agonist, an orexin antagonist, a melanin concentrating hormone antagonist, a galanin antagonist, a CCK agonist, a GLP-1 agonist, a corticotropin-releasing hormone agonist or a NPY, antagonist. Moieties that facilitate detection include radionuclides, luminescent groups, fluorescent groups and enzymes, all of which may be associated with a compound via standard methods.

For detection purposes, as discussed in more detail below, compounds provided herein may be isotopically-labeled or radiolabeled. Such compounds are identical to those recited in Formula I, but for the fact that one or more atoms are replaced by an atom having an atomic mass or mass number different from the atomic mass or mass number usually found in nature. Examples of isotopes that can be incorporated into compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Other moieties that may be associated with an active compound include carriers. Such substances may modulate bioavailability or stability of the compound. Representative carriers include, for example, molecules such as albumin, polylysine, polyamidoamines, peptides, proteins, polystyrene, polyacrylamide, lipids, ceramide and biotin, solid support materials such as beads and microparticles comprising, for example, polylactate polyglycolate, poly(lactide-co-glycolide), polyacrylate, latex, starch, cellulose or dextran.

Preparation of NPY5 Receptor Modulators

Substituted derivatives of 2-cyclohexyl-4-phenyl-1H-imidazole may generally be prepared using standard synthetic methods, which are well known to those of ordinary skill in the art of organic synthesis. Representative methods are described below, and within Examples 1–9. Such methods may be combined with other known synthetic methods and variations thereon (e.g., modification of starting materials) that will be apparent to those of ordinary skill in the art, to generate all compounds provided herein.

By way of example, a synthetic route similar to those shown in any one of Schemes 1–3 (below) may be used. Within these Schemes, "coupling" refers to a suitable coupling reagent such as, but not limited to BOP or EDCI. These coupling reactions can be carried out at ambient or elevated temperatures using various solvents including, but not limited to, methylene chloride, DMF and THF. Coupling reactions can be used to prepare the compounds encompassed by general structures 1-C (Scheme 1) and 3-D (Scheme 3). In Scheme 1, following coupling, compound 1-C may be converted directly to compound 1-E (when $R_1$ is H). Alternatively, to generate compounds with $R_1$ groups that are not H, synthesis may proceed via compound 1-D.

In Scheme 2, "deprotection" refers to the process of removal of benzyl carbamate group. This deprotection can be carried out in a number of ways well known to those skilled in the art of organic synthesis including, but not limited to, catalytic hydrogenation, acid hydrolysis and base hydrolysis. Deprotection can be used to prepare the compounds encompassed in general structure 2-B.

In Scheme 2, "reduction" refers to the process of synthetic transformation wherein an amide moiety is converted to an amine. Such a transformation can be used to prepare compounds of general structure 2-D. Suitable reductive reagents include, but are not limited to, $BH_3$, $LiAlH_4$ and $LiBH_3CN$.

In Scheme 2, "reductive amination" refers to the process of synthetic transformation wherein a primary amine is converted to a secondary amine by reaction with a suitable aldehyde or ketone. Such a transformation can be carried out in a number of ways well known to those skilled in the art of organic synthesis. Suitable reducing reagents include, but are not limited to, $BH_3$, $NaBH_4$, $NaiBH_3CN$ and acid $NaBH(OAc)_3$. This reaction can be used to prepare the compounds encompassed in general structure 2-E.

In Scheme 3, "hydrolysis" refers to the synthetic transformation wherein an ester moiety is converted to a carboxylic acid group. Such a transformation can be used to prepare compounds of general structure 3-B. The reagents suitable for carrying out this transformation are well known to those skilled in the art of organic synthesis and include, but are not limited to, KOH, NaOH and HCl.

In Scheme 3, "oxidation" refers to the synthetic transformation wherein an alcohol moiety is converted to a ketone group. Such a transformation can be used to prepare compounds of general structure 3-E. Oxidation methods are well known to those skilled in the art of organic synthesis and include, but are not limited to, Swern oxidation and Dess-Martin oxidation.

Scheme 1
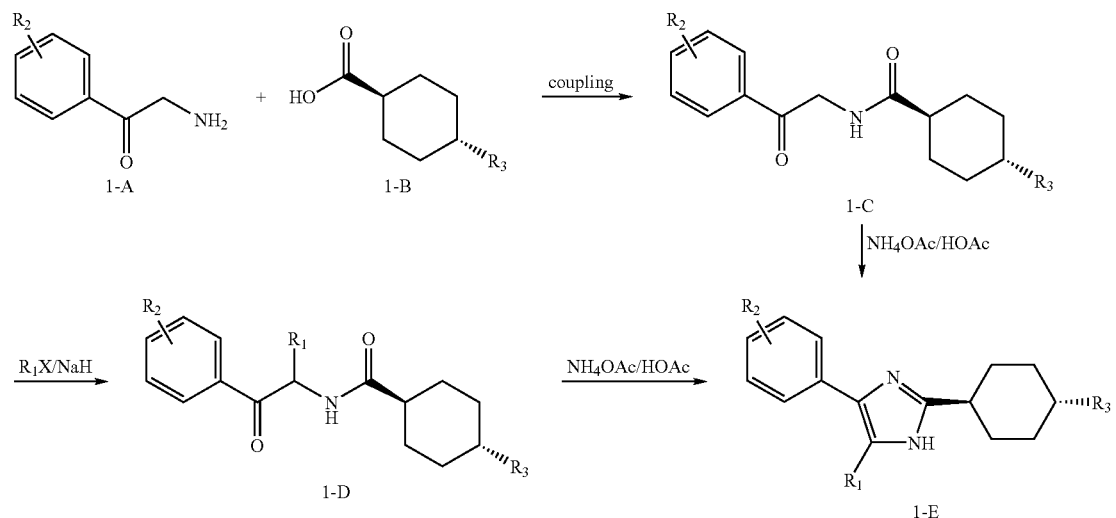
Scheme 2
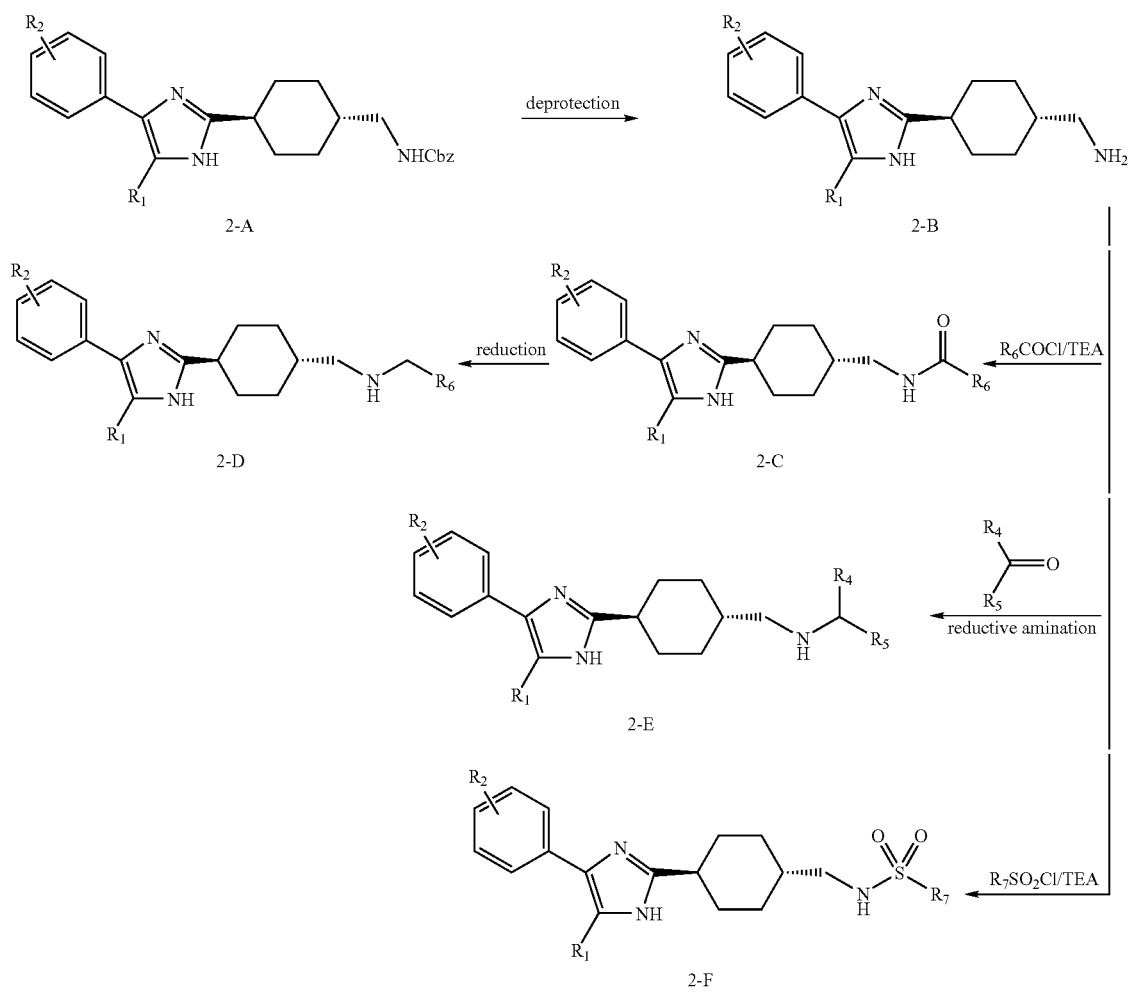

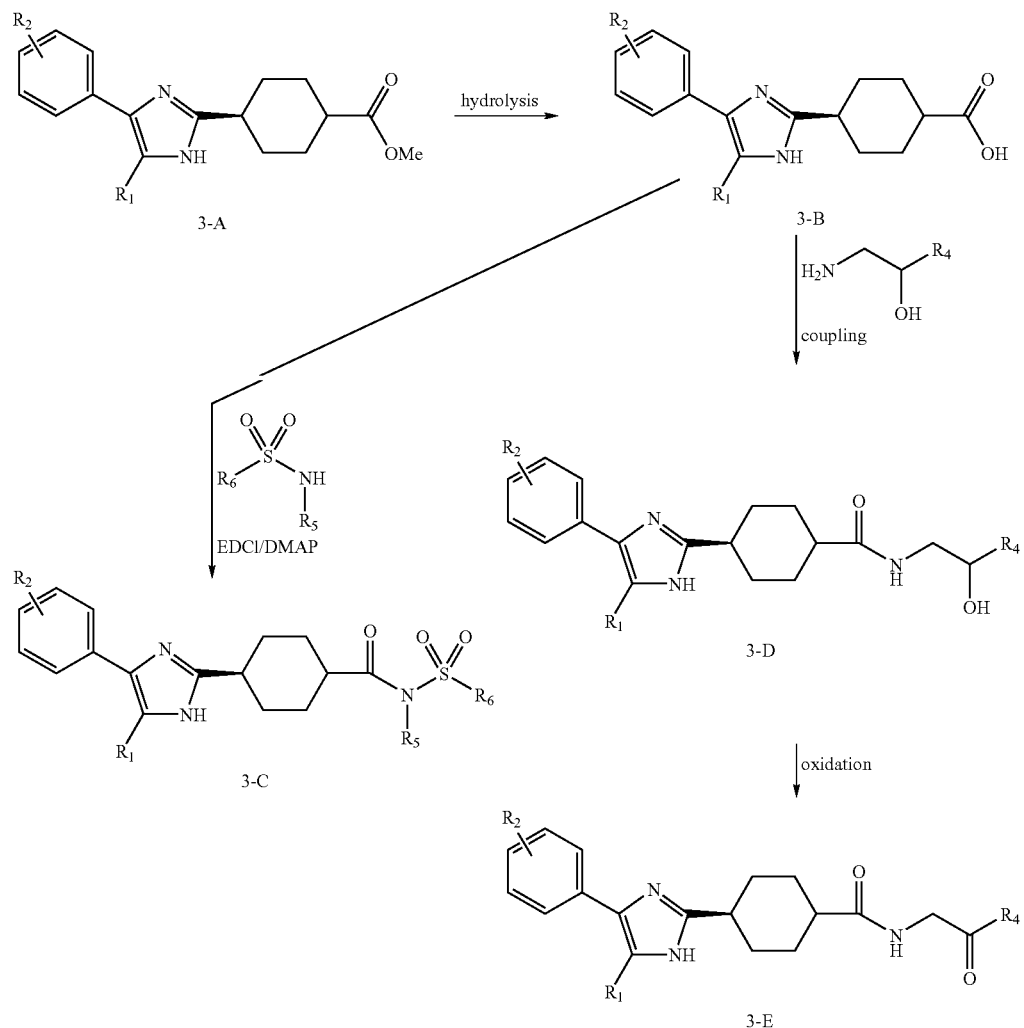

Scheme 3

In certain situations, the compounds of this invention may contain one or more asymmetric carbon atoms, so that the compounds can exist in different stereo-isomeric forms. These compounds can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

As noted above, the present invention encompasses pharmaceutically acceptable salts of the compounds described herein. As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). Accordingly, the present disclosure should be construed to include all pharmaceutically acceptable salts of the compounds specifically recited.

A wide variety of synthetic procedures are available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

The present invention also encompasses prodrugs of the compounds of Formula I, which may be modified (either in routine manipulation or in vivo) to generate an active agent encompassed by Formula I. Such prodrugs may be prepared by modifying functional groups present in the compounds in such a way that the modifications are cleaved to the parent compounds. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein. Preferred prodrugs include acylated derivatives. Those of ordinary skill in the art will recognize various synthetic methods that may be employed to prepare prodrugs of the compounds provided herein.

Additional moieties may be associated with a compound using any suitable procedure. Covalent linkage may generally be achieved using suitable functional groups (e.g., hydroxyl, carboxyl, sulfhydryl or amino groups) on the compound and the moiety to be attached. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. The use of bifunctional, multifunctional and/or cleavable linkers may also be desirable for certain applications. Such linkers are well known in the art. Compounds associated with carriers may be covalently linked or, preferably, such association does not involve covalent interaction and is achieved by mixing.

Compounds may be radiolabeled by carrying out their synthesis using precursors comprising at least one atom that is a radioisotope (i.e., an isotopically labeled reagent is substituted for a non-isotopically labeled reagent). Numerous radioisotopes are readily available, including isotopes of hydrogen, carbon, nitrogen, oxygen, phosphorous, sulfur, iodine, fluorine and chlorine, such as $^{14}C$, $^{3}H$, $^{35}S$ or $^{125}I$. Synthesis of radiolabeled compounds may be conveniently performed by a radioisotope supplier specializing in custom synthesis of radiolabeled probe compounds, such as Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif. Tritium labeled compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations may also be performed as a custom radiolabeling by any of the suppliers listed above using the compound as substrate. In addition, certain precursors may be subjected to tritium-halogen exchange with tritium gas, tritium gas reduction of unsaturated bonds, or reduction using sodium borotritide, as appropriate.

Pharmaceutical Compositions

The present invention also provides pharmaceutical compositions comprising NPY5 receptor modulators, together with at least one physiologically acceptable carrier or excipient. Such compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs).

If desired, other active ingredients may also be included. For example, compositions intended for the treatment of eating disorders, particularly obesity and bulimia nervosa, may further comprise an agent such as sibutramine, dexenfluramine, leptin, a growth hormone secretagogue, a melanocortin agonist, a beta-3 agonist, a 5HT-2 agonist, an orexin antagonist, a melanin concentrating hormone antagonist, a galanin antagonist, a CCK agonist, a GLP-1 agonist and/or a corticotropin-releasing hormone agonist or a $NPY_1$ antagonist.

Pharmaceutical compositions may be formulated for any appropriate manner of administration, including for example, topical, oral, nasal, rectal or parenteral administration. The term parenteral as used herein includes subcutaneous injections, intradermal, intravascular (e.g., intravenous), intramuscular, spinal, intracranial, intrathecal, intraperitoneal injection or like injection or infusion techniques. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further contain one or more components such as sweetening agents, flavoring agents, coloring agents and preserving agents in order to provide appealing and palatable preparations. Tablets contain the active ingredient(s) in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules in which the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active materials in admixture with excipients suitable for the manufacture of aqueous suspensions. Such excipients are suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents, and/or one or more sweetening agents, such as sucrose or saccharin.

Oily suspensions may be formulated by suspending the active ingredients in a vegetable oil (e.g., arachis oil, olive oil, sesame oil or coconut oil), or in a mineral oil such as liquid paraffin. The oily suspensions may also contain a thickening agent such as beeswax, hard paraffin or cetyl alcohol. Sweetening agents, such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and/or one or more preservatives. Suitable dispersing or wetting agents and suspending agents are exemplified by those already mentioned above. Additional excipients, such as sweetening, flavoring and/or coloring agents, may also be present.

Pharmaceutical compositions may also be in the form of oil-in-water emulsions. The oily phase may be a vegetable oil (e.g., olive oil or arachis oil), or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents, such as those mentioned above. Among the acceptable vehicles and solvents that may be employed are water, 1,3-butanediol, Ringer's solution and isotonic sodium chloride solution. In addition, sterile, fixed oils may be used as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can also be dissolved in the vehicle.

Modulators may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

For administration to non-human animals, the composition may also be added to animal feed or drinking water. It may be convenient to formulate animal feed and drinking water compositions so that the animal takes in an appropriate quantity of the composition along with its diet. It may also be convenient to present the composition as a premix for addition to feed or drinking water.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon the site of implantation, the rate and expected duration of release and the nature of the condition to be treated or prevented.

Modulators are generally present within a pharmaceutical composition in a therapeutically effective amount. A therapeutically effective amount is an amount that results in a discernible patient benefit, such as increased healing of a disease or disorder associated with pathogenic NPY5 receptor activation, as described herein. A preferred concentration is one sufficient to inhibit the binding of ligand (i.e., NPY and/or PYY) to NPY5 receptor in vitro. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing, and procedures that are well known in the art.

Pharmaceutical compositions may be packaged for treating disorders responsive to NPY5 receptor modulation (e.g., treatment of eating disorders such as obesity or bulimia, psychiatric disorders, cardiovascular disorders such as hypertension or diabetes). Packaged pharmaceutical compositions generally include a container holding a therapeutically effective amount of at least one NPY5 receptor modulator as described herein and instructions (e.g., labeling) indicating that the contained composition is to be used for treating a disorder associated with NPY5 receptor activation in the patient.

Methods of Use

Within certain aspects, the present invention provides methods for inhibiting the development of a disease or disorder associated with NPY5 receptor activation. In other words, therapeutic methods provided herein may be used to treat an existing disease or disorder, or may be used to prevent or delay the onset of such a disease in a patient who is free of a detectable disease or disorder that is associated with NPY5 receptor activation. As used herein, a disease or disorder is "associated with NPY5 receptor activation" if it is characterized by inappropriate stimulation of NPY5 receptor, regardless of the actual amount of NPY present locally. Such conditions include, for example, eating disorders (such as obesity, anorexia, bulimia and metabolic disorders), diseases related to the central nervous system (such as psychiatric disorders), diseases related to abnormal hormone release (such as diabetes) and cardiovascular disorders. Diseases related to the central nervous system include cerebral infarction, neurodegeneration, epilepsy, stroke and conditions related to stroke, cerebral vasospasm and hemorrhage, depression, anxiety, schizophrenia and dementia, as well as conditions related to pain or nociception. Diseases related to abnormal hormone release include conditions associated with abnormal release of luteinizing hormone, growth hormone, insulin and prolactin. Cardiovascular disorders include any disorders or diseases pertaining to the heart, blood vessels or the renal system, such as hypertension, vasospasm, heart failure, shock, cardiac hypertrophy increased blood pressure, angina, myocardial infarction, sudden cardiac death, arrhythmia, peripheral vascular disease, and abnormal renal conditions such as impaired flow of fluid, abnormal mass transport or renal failure. Other diseases and disorders associated with NPY5 receptor activation include conditions related to increased sympathetic nerve activity (e.g., during or after coronary artery surgery, and operations and surgery in the gastrointestinal tract); diseases related to abnormal gastrointestinal motility and secretion (such as different forms of ileus, urinary incontinence and Crohn's disease); diseases related to sexual dysfunction and reproductive disorders; conditions or disorders associated with inflammation; and respiratory diseases, such as asthma and conditions related to asthma and bronchoconstriction. The above conditions may be diagnosed and monitored using criteria that have been established in the art. Patients may include humans, domesticated companion animals (pets, such as dogs) and livestock animals, with dosages and treatment regimes as described above.

Frequency of dosage may vary depending on the compound used and the particular disease to be treated or prevented. In general, for treatment of most disorders, a dosage regimen of 4 times daily or less is preferred. For the treatment of eating disorders, including obesity, a dosage regimen of 1 or 2 times daily is particularly preferred. For the treatment of impotence a single dose that rapidly reaches effective concentrations is desirable. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Within separate aspects, the present invention provides a variety of in vitro uses for the compounds provided herein. For example, such compounds may be used as probes for the detection and localization of NPY5 receptors, in samples such as tissue sections, as positive controls in assays for receptor activity, as standards and reagents for determining the ability of a candidate agent to bind to NPY5 receptor, or as radiotracers for positron emission tomography (PET) imaging or for single photon emission computerized tomography (SPECT). Such assays can be used to characterize NPY5 receptors in living subjects.

Within methods for determining the presence or absence of NPY5 receptor in a sample, a sample may be incubated with a compound as provided herein under conditions that permit binding of the compound to NPY5 receptor. The amount of compound bound to NPY5 receptor in the sample is then detected. For example, a compound may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method for the label employed (e.g., autoradiography or scintillation counting for radiolabeled compounds; spectroscopic methods may be used to detect dyes, luminescent groups and fluorescent groups). Detection assays, including receptor autoradiography (receptor mapping) of NPY5 receptors in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell culture and cell separation methods. For example, modulators may be linked to the interior surface of a tissue culture plate or other cell culture support, for use in immobilizing NPY5-expressing cells for screens, assays and growth in culture. Such linkage may be performed by any suitable technique, such as the methods described above, as well as other standard techniques. Modulators may also be used to facilitate cell identification and sorting in vitro, permitting the selection of cells expressing NPY5. Preferably, the modulator(s) for use in such methods are labeled as described herein. Within one preferred embodiment, a modulator linked to a fluorescent marker, such as fluorescein, is contacted with the cells, which are then analyzed by fluorescence activated cell sorting (FACS).

Within other aspects, methods are provided for modulating binding of an NPY5 receptor ligand (such as NPY or PYY) to NPY5 receptor in vitro or in vivo, comprising contacting a sufficient amount of NPY5 receptor with a modulator provided herein, under conditions suitable for binding of NPY5 to the receptor. Preferably, within such methods, NPY and/or PYY binding to receptor is inhibited by the modulator. The NPY5 receptor may be present in solution, in a cultured or isolated cell preparation or within a patient. In general, the amount of compound contacted with the receptor in vivo should be sufficient to modulate NPY binding to NPY5 receptor in vitro within, for example, a ligand binding assay as described in Example 11. $NPY_5$ receptors used to determine in vitro binding may be obtained from a variety of sources, for example from preparations of rat brain or from cells expressing cloned human $NPY_5$ receptors.

Also provided herein are methods for modulating the signal-transducing activity of NPY5 receptor, by contacting an NPY5 receptor, either in vivo or in vitro, with a sufficient amount of an NPY5 receptor modulator as described above, under conditions suitable for binding of NPY to NPY5 receptor. The NPY5 receptor may be present in solution, in a cultured or isolated cell preparation or within a patient. In general, the amount of a modulator that is sufficient to alter the signal-transducing activity of NPY5 receptor may be determined via a NPY5 receptor signal transduction assay, such as the assay described in Example 12.

The following Examples are offered by way of illustration and not by way of limitation. Unless otherwise specified all reagents and solvent are of standard commercial grade and are used without further purification.

EXAMPLE

Example 1

Preparation of Cyclopentyl-{4-[4-(3-trifluoromethyl-phenyl)-1H-imidazol-2-yl]-cyclohexylmethyl}-amine This Example illustrates the preparation of a representative 2-cyclohexyl-4-phenyl-1H-imidazole derivative having the structure:

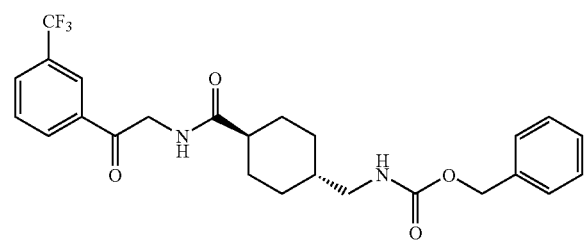

To a solution of 2-Amino-1-(3-trifluoromethyl-phenyl)-ethanone hydrochloride (3.4 g, 0.0144 mol (prepared according to the procedure of Leclerc and Bizec (1980) *J. Med. Chem.* 23:783–744) and 4-(Benzyloxycarbonylaminomethyl)-cyclohexanecarboxylic acid (4.2 g, 0.0144 mol; for a preparation of this reagent see e.g., Svahn et. al. (1986) *J. Med. Chem.* 29:448–453) in DMF, Benzotriazol-1-yloxytris (dimethylamino)phosphonium hexafluorophosphate (BOP reagent, 6.4 g, 0.0144 mol) was added, followed by triethylamine (4.0 mL, 0.0289 mol). The reaction was stirred overnight and then poured into water to produce a thick precipitate. The solid was collected on a sintered glass funnel and washed consecutively with $H_2O$, 3N HCl (2×), $H_2O$, $NaHCO_3$ solution (2×) and $H_2O$. The filter cake was air dried, added to a 500 mL round bottom flask with toluene and concentrated under reduced pressure. Additional toluene (200 mL) was added and the mixture was concentrated again under reduced pressure to yield {4-[2-Oxo-2-(3-trifluoromethyl-phenyl)-ethylcarbamoyl]-cyclohexylmethyl}-carbamic acid benzyl ester as a solid. $^1$H NMR (DMSO-d6): δ0.8–0.93 (m, 2H), 1.2–1.37 (m, 3H), 1.71 (br s, 4H), 2.14 (t, 1H), 2.84 (br s, 2H), 4.57 (br s, 2H), 4.99 (s, 2H), 7.2–7.38 (m, 5H), 7.77(t, 1H), 8.01 (d, J=8.0 Hz, 1H), 8.14–8.26 (m, 3H). MS 477 (M+H)$^+$

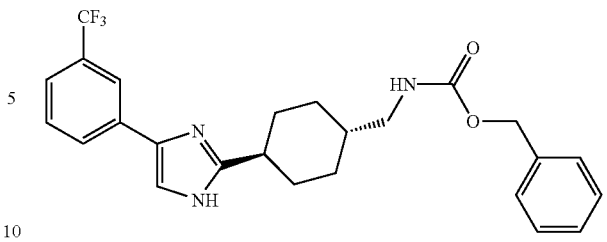

B. Ammonium acetate (26 g, 0.34 mol) was added to a solution of {4-[2-Oxo-2-(3-trifluoromethyl-phenyl)-ethyl-carbamoyl]-cyclohexylmethyl}-carbamic acid benzyl ester (5.4 g, 0.0113 mol) in acetic acid. The resulting homogeneous mixture was refluxed overnight and then concentrated under reduced pressure. The residue was partitioned between 10% NaOH and EtOAc (1:1) and the EtOAc layer was washed with 10% NaOH (3×) and brine. The EtOAc was dried ($Na_2SO_4$) and concentrated under reduced pressure to give {4-[4-(3-Trifluoromethyl-phenyl)-1H-imidazol-2-yl]-cyclohexylmethyl}-carbamic acid benzyl ester. $^1$H NMR (CDCl$_3$): δ 1.02–1.18 (m, 2H), 1.46–1.62 (m, 3H), 1.86–1.96 (m, 2H), 2.12–2.21 (m, 2H), 2.74 (m, 1H), 3.10 (t, J=6 Hz, 2H), 4.91 (t, 1H, N—H), 5.10 (s, 2H), 7.22 (s, 1H), 7.32–7.37 (m, 5H), 7.45 (d, J=4.9 hz, 2H), 7.87 (m, 1H), 7.95 (s, 1H). MS 458 (M+H)$^+$

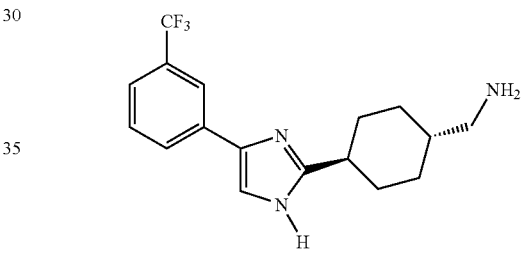

C. An ethanolic solution of {4-[4-(3-Trifluoromethyl-phenyl)-1H-imidazol-2-yl]-cyclohexylmethyl}-carbamic acid benzyl ester (4.15 g, 0.0091 mol) and 10% Pd/Carbon (400 mg) was shaken overnight under 55 psi of hydrogen in a Paar apparatus. The mixture was filtered through celite and concentrated under reduced pressure to give a foam, which was triturated with EtOAc/Hexanes/MeOH to produce C-{4-[4-(3-trifluoromethyl-phenyl)-1H-imidazole-2-yl]-cyclohexyl}-methylamine as a filterable solid. $^1$H NMR (DMSO-d6): δ 0.93–1.05 (m, 2H), 1.30–1.4 (m, 2H), 1.42–1.55 (m, 2H), 1.85 (d, J=12.8 Hz, 2H), 1.99 (d, J=11.6 Hz, 2H), 2.4–2.5 (m, 1H), 2.56–2.66 (m, 1H), 7.43–7.48 (m, 1H), 7.50–7.55 (m, 1H), 7.63 (s, 1H), 7.99 (d, J=7.9 Hz, 1H), 8.02 (s, 1H). MS 324 (M+H)$^+$

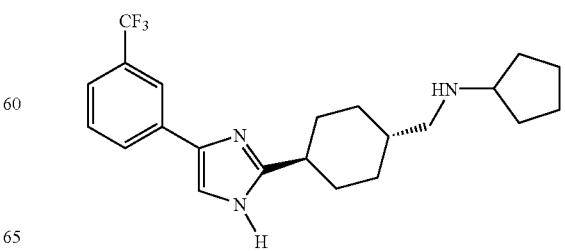

D. C-{4-[4-(3-trifluoromethyl-phenyl)-1H-imidazole-2-yl]-cyclohexyl}-methylamine (217 mg, 0.672 mmol) was dissolved in a mixture of dichloroethane and THF (~2:1). Cyclopentanone (62 mg, 0.74 mmol) was added to the reaction mixture, followed by acetic acid (0.672 mmol). Sodium triacetoxyborohydride was added and the reaction was stirred overnight at room temperature. The reaction mixture was concentrated under reduced pressure and partitioned between ethyl acetate and 10% NaOH. The ethyl acetate layer was dried (Na$_2$SO$_4$), concentrated under reduced pressure, and purified using preparative plate chromatography (MeOH/CH$_2$Cl$_2$ eluent) to generate cyclopentyl-{4-[4-(3-trifluoromethyl-phenyl)-1H-imidazol-2-yl]-cyclohexylmethyl}-amine.

Example 2

Preparation of Ethyl-{4-[4-(3-trifluoromethyl-phenyl)-1H-imidazole-2-yl]cyclohexylmethyl}-amine This Example illustrates the preparation of a representative 2-cyclohexyl-4-phenyl-1H-imidazole derivative having the structure:

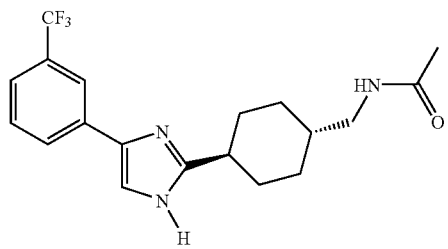

A. C-{4-[4-(3-trifluoromethyl-phenyl)-1H-imidazole-2-yl]-cyclohexyl}-methylamine (326 mg, 1.0 mmol, from Example 1C) and TEA (102 mg, 1.0 mmol) were dissolved in CH$_2$Cl$_2$/THF (1:1) and brought to 0° C. with an ice bath. Acetyl chloride (79 mg, 1.0 mmol) was added to the reaction mixture slowly and the ice bath was removed. After 2 hours, the solution was diluted with CH$_2$Cl$_2$, added to a separatory funnel and washed with 10% NaOH (3×). The solution was dried (Na$_2$SO$_4$), concentrated under reduced pressure, and the residue purified using flash chromatography (5%→10% MeOH/CH$_2$Cl$_2$) to give (N-{4-[4-(3-Trifluoromethyl-phenyl)-1H-imidazol-2-yl]-cyclohexylmethyl}-acetamide.

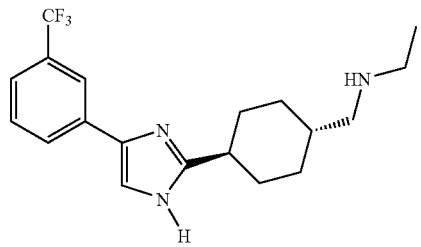

B. To a solution of (N-{4-[4-(3-Trifluoromethyl-phenyl)-1H-imidazol-2-yl]-cyclohexylmethyl}-acetamide (207 mg, 0.57 mmol, from Example 2A) in THF, 3 equivalents of borane dimethylsulfide (2M in THF) was added, and the solution stirred overnight at room temperature. One volume of MeOH was added to the reaction mixture, and the mixture was concentrated under reduced pressure. 50 mL of 3N HCl was added, and the mixture was warmed for 5 minutes. After washing the solution with ether, the solution was made basic with NaOH and extracted with ethyl acetate. The solution was dried (Na$_2$SO$_4$), concentrated under reduced pressure, and purified using preparative plate chromatography to give Ethyl-{4-[4-(3-trifluoromethyl-phenyl)-1H-imidazole-2-yl] cyclohexylmethyl}-amine.

Example 3

Preparation of Cyclopentyl-{4-[5-methyl-4-(3-trifluoromethyl-phenyl)-1H-imidazol-2-yl]-cyclohexylmethyl}-amine This Example illustrates the preparation of a representative 2-cyclohexyl-4-phenyl-1H-imidazole derivative having the structure:

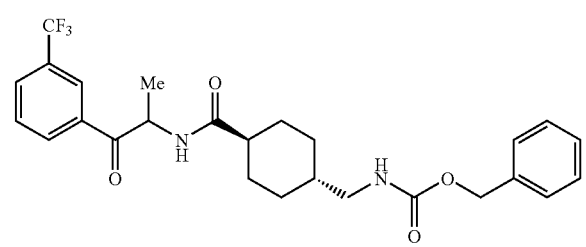

A. This compound was prepared using a procedure similar to the one described by Moriya et. al. (J. Med. Chem. (1986) 29:333–341) for the alkylation of α-(N-acylamino) ketones: {4-[2-Oxo-2-(3-trifluoromethyl-phenyl)-ethylcarbamoyl]-cyclohexylmethyl}-carbamic acid benzyl ester (From Example 1A; 584 mg, 1.23 mmol) was dissolved in dry DMF and brought to −40° C. using a dry ice/acetonitrile cooling bath. NaH (61 mg, 1.53 mmol, 60% dispersion in oil) was added in one portion and the mixture was stirred for 15 minutes. MeI (192 mg, 1.35 mmol) was added all at once, the cooling bath was removed and the reaction mixture was allowed to come to room temperature. An excess of saturated aqueous NH$_4$Cl solution was added and the resulting mixture extracted with EtOAc. The EtOAc layer was washed sequentially with 3N HCl, NaHCO$_3$ (sat'd), and brine. The solution was dried (Na$_2$SO$_4$) and concentrated under reduced pressure to give {4-[1-Methyl-2-oxo-2-(3-trifluoromethyl-phenyl)-ethylcarbamoyl]-cyclohexylmethyl}-carbamic acid benzyl ester.

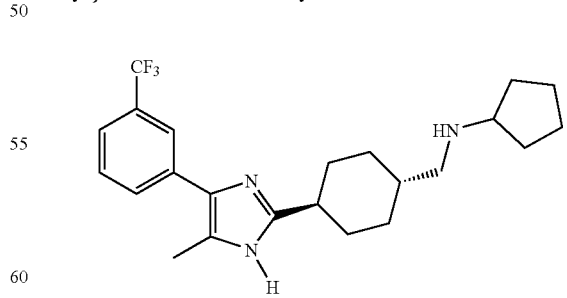

B. Using procedures analogous to those described in Examples 1B to 1D, the compound from Example 3A was converted to Cyclopentyl-{4-[5-methyl-4-(3-trifluoromethyl-phenyl)-1H-imidazol-2-yl]-cyclohexylmethyl}-amine.

Example 4

Preparation of N-{4-[4-(3-Chloro-phenyl)-1H-imidazol-2-yl]cyclohexylmethyl}-benzenesulfonamide This Example illustrates the preparation of a representative 2-cyclohexyl-4-phenyl-1H-imidazole derivative having the structure:

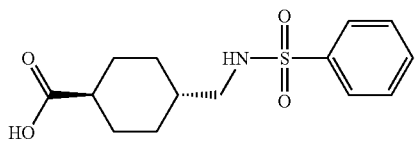

A. trans-4-(Aminomethyl)cyclohexane carboxylic acid (15.2 g, 0.097 mol) was dissolved in a 2N NaOH solution (96.5 mL, 2 equivalents). The solution was brought to 10° C., benzenesulfonyl chloride (17.1 g, 0.097 mol) was added dropwise and then the mixture was stirred overnight at room temperature. The mixture was diluted with water, the solution was washed with ether, and then the aqueous portion was acidified with 12N HCl to give an oily precipitate. The precipitate was extracted with $CH_2Cl_2$, and the extracts were dried ($Na_2SO_4$) and concentrated under reduced pressure to give trans-4-(Benzenesulfonylamino-methyl)-cyclohexanecarboxylic acid as a white solid.

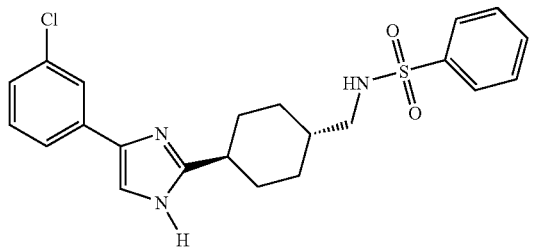

B. Using procedures analogous to those described in Examples 1A and 1B, the compound from Example 5A was converted to N-{4-[4-(3-Chloro-phenyl)-1H-imidazol-2-yl]cyclohexylmethyl}-benzenesulfonamide.

Example 5

Preparation of N-{4-[4-(3-Cyano-phenyl)-1H-imidazol-2-yl]-cyclohexylmethyl}-acetamide This Example illustrates the preparation of a representative 2-cyclohexyl-4-phenyl-1H-imidazole derivative having the structure:

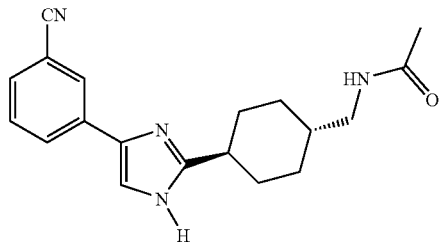

A. A solution of N-{4-[4-(3-Bromo-phenyl)-1H-imidazol-2-yl]-cyclohexylmethyl}-acetamide (54 mg, 0.14 mmol, prepared using procedures described above), $ZnCN_2$ (17 mg, 0.14 mmol), and tetrakis(triphenylphosphine)palladium(0) (15 mg) was heated to 150° C. for 8 hours. The solution was cooled, diluted with water and extracted with ethyl acetate. The ethyl acetate was washed with 10% NaOH (3×) and brine, dried ($Na_2SO_4$) and concentrated under reduced pressure. The crude product was purified using preparative plate chromatography (MeOH/$CH_2Cl_2$) to give N-{4-[4-(3-Cyano-phenyl)-1H-imidazol-2-yl]-cyclohexylmethyl}-acetamide.

Example 6

Preparation of trans-N-[(4-methylphenyl)sulfonyl] (4-{4-[3-(trifluoromethyl)phenyl]imidazol-2-yl}cyclohexyl)carboxamide This Example illustrates the preparation of a representative 2-cyclohexyl-4-phenyl-1H-imidazole derivative having the structure:

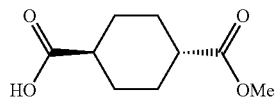

A. trans-Cyclohexane-1,4-dicarboxylic acid dimethyl ester (34.2 g, 0.171 mol) was dissolved in 400 mL of anhydrous methanol and the solution brought to reflux. Slowly (dropwise), a solution of KOH (11.2 g, 0.171 mol, 85% purity) in dry methanol was added to the refluxing solution. The solution continued to reflux for 5 hours, and was then cooled and concentrated under reduced pressure to give a white solid. Water was added to dissolve most of the solid, and the aqueous mixture was washed with ether (3×) in a separatory funnel. The aqueous layer was brought to pH ~6, the resulting white precipitate was collected via filtration and washed (1×) with a small amount of water. Air drying afforded trans-cyclohexane-1,4-dicarboxylic acid monomethyl ester as a white solid.

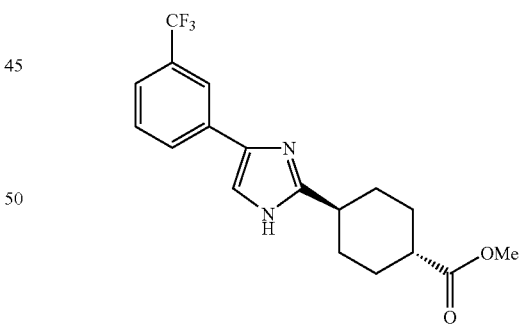

B. The solution of 2-amino-1-(3-trifluoromethyl-phenyl)-ethanone hydrochloride (50.2 mmol), trans-cyclohexane-1,4-dicarboxylic acid monomethyl ester (50.2 mmol), triethylamine (100.4 mmol) and BOP (50.2 mmol) in DMF (100 mL) was stirred overnight at room temperature. The mixture was diluted with water, extracted with EtOAc, washed with saturated $NaHCO_3$ and brine, dried over $Na_2SO_4$, and concentrated under vacuum. The residue was triturated with ether and the precipitate was collected. The precipitate was mixed with $NH_4OAc$ (930 mmol) and 200 ml of AcOH and refluxed overnight. The excess AcOH was removed and purification by flash chromatography (95:5 CH$_2$Cl$_2$/MeOH) gave trans-4-[4-(3-trifluoromethyl-phenyl)-1H-imidazol-2-yl]-cyclohexyl-carboxylic acid methyl ester.

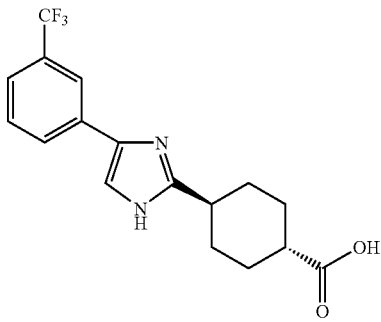

C. To a solution of trans-4-[4-(3-trifluoromethyl-phenyl)-1H-imidazol-2-yl]-cyclohexylcarboxylic acid methyl ester (13.4 mmol) in 50 ml of THF was added LiOH (80.3 mmol) in 30 ml of H$_2$O. The mixture was stirred at 60° C. for 2 hours, then concentrated, diluted with H$_2$O and washed with ether. The aqueous layer was acidified to pH 5-6, extracted with EtOAc, dried over Na$_2$SO$_4$, and concentrated to give trans-4-[4-(3-trifluoromethyl-phenyl)-1H-imidazol-2-yl]-cyclohexyl-carboxylic acid.

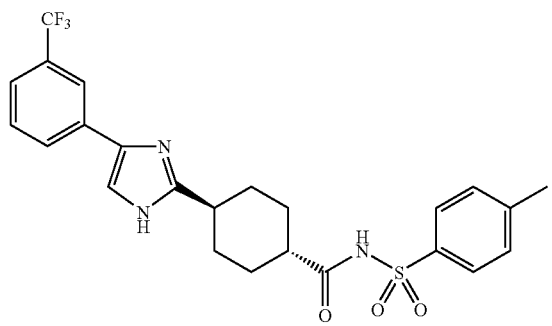

D. To an ice-water cooled mixture of trans-4-{4-[3-(trifluoromethyl)phenyl]imidazol-2-yl}cyclohexanecarboxylic acid (1.48 mmol), 4-methylbenzenesulfonamide (1.48 mmol), and DMAP (1.48 mmol) in dichloromethane (10 mL) under nitrogen, EDC (1.48 mmol) was added. The mixture was stirred at room temperature overnight, concentrated and chromatographed on silica gel (19:1 EtOAc-MeOH eluent) to give trans-N-[(4-methylphenyl)sulfonyl](4-{4-[3-(trifluoromethyl)phenyl]-imidazol-2-yl}cyclohexyl)carboxamide.

Example 7

Preparation of trans-4-[4-(3-bromo-phenyl)-1H-imidazol-2-yl]-cyclohexane-carboxylic acid (2-hydroxy-propyl)amide This Example illustrates the preparation of a representative 2-cyclohexyl-4-phenyl-1H-imidazole derivative having the structure:

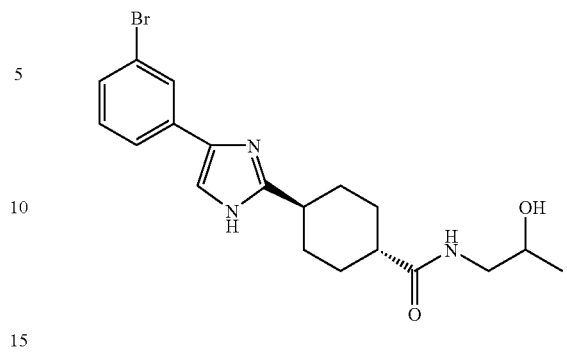

The solution of trans-4-[4-(3-bromo-phenyl)-1H-imidazol-2-yl]-cyclohexyl-carboxylic acid (1.22 mmol), 2-hydroxy-propylamine(3.65 mmol) and BOP (1.22 mmol) in DMF (6 mL) was stirred overnight at room temperature. The mixture was diluted with water, extracted with EtOAc, washed with saturated NaHCO$_3$, dried over Na$_2$SO$_4$, and concentrated under vacuum. The residue was purified with flash chromatography (90:10:1 CH$_2$Cl$_2$/MeOH/NH$_4$OH) to give trans-4-[4-(3-bromo-phenyl)-1H-imidazol-2-yl]-cyclohexane-carboxylic acid (2-hydroxy-propyl) amide.

Example 8

Preparation of trans-4-[4-(3-bromo-phenyl)-1H-imidazol-2-yl]-cyclohexane-carboxylic acid (2-oxo-propyl)amide This Example illustrates the preparation of a representative 2-cyclohexyl-4-phenyl-1H-imidazole derivative having the structure:

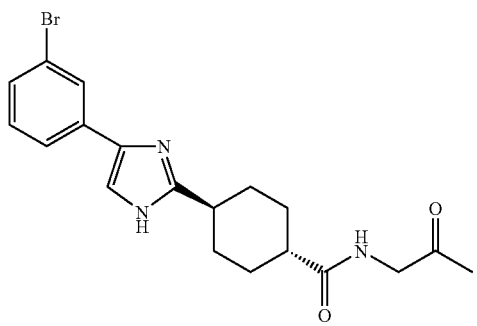

To a cooled solution (−78° C. to −60° C.) of oxalyl chloride (0.12 mmol) in CH$_2$Cl$_2$ (5 mL), DMSO (0.25 mmoL) was added dropwise. The mixture was stirred for 2 minutes, and then trans-4-[4-(3-bromo-phenyl)-1H-imidazol-2-yl]-cyclohexane-carboxylic acid (2-hydroxy-propyl) amide (0.12 mmol) in 2 ml of CH$_2$Cl$_2$ was added. The mixture was stirred for 15 minutes at the same temperature following the addition of TEA (0.60 mmol). The mixture was stirred for another 5 minutes, warmed to room temperature and diluted with water. The organic layer was isolated, dried over Na$_2$SO$_4$, concentrated under vacuum, and purified with flash chromatography (90:10:1 CH$_2$Cl$_2$/MeOH/NH$_4$OH) to give trans-4-[4-(3-bromo-phenyl)-1H-imidazol-2-yl]-cyclohexane-carboxylic acid (2-oxo-propyl) amide.

Example 9

Preparation of Pyridine-3-sulfonic acid trans-{4-[4-(3-trifluoromethyl-phenyl)-1H-imidazol-2-yl]-cyclohexylmethyl}-amide This Example illustrates the preparation of a representative 2-cyclohexyl-4-phenyl-1H-imidazole derivative having the structure:

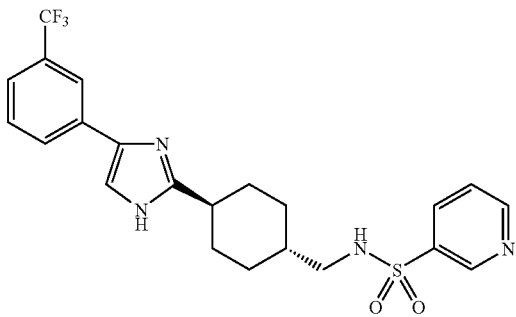

Pyridine-3-sulfonyl chloride (0.34 mmol) was added to a solution of C-{4-[4-(3-trifluoromethyl-phenyl)-1H-imidazol-2-yl]-cyclohexyl}-methylamine (0.31 mmol) and triethylamine (0.62 mmol) in $CH_2Cl_2$ (5 mL). The mixture was stirred overnight at room temperature, diluted with $CH_2Cl_2$, washed with saturated $NaHCO_3$, dried over $Na_2SO_4$, and concentrated under vacuum. The residue was purified by flash chromatography (90:10 $CH_2Cl_2$/MeOH) to give Pyridine-3-sulfonic acid trans-{4-[4-(3-trifluoromethyl-phenyl)-1H-imidazol-2-yl]-cyclohexylmethyl}-amide.

Example 10

Preparation of NPY5 Chimeric Receptors

This Example illustrates the preparation of a representative NPY5 receptor for use in assays described herein.

A. DNA Clones Encoding NPY Receptors

Human Y5 receptor was cloned from genomic DNA using a 5' Primer TTTTGGTTGCTGACAAATGTC (SEQ ID NO: 1) and a 3' Primer CCTTGGTAAACAGTGAGAATTATTAC (SEQ ID NO: 2). The full length PCR product was initially cloned into the vector pCR 2.1 (Invitrogen, Carlsbad, Calif.) and then subcloned into pBluescript SK Minus (pBSSKM, Stratagene, La Jolla Calif.). This was designated pNN32.

Bases 197 to 1433 of Y1 receptor (Genbank Accession number M88461, SEQ ID NO: 3) were subcloned into pBSSKM and designated pNN22. A pBSSKM clone encoding a 5' truncated form of the Y5 receptor was made which deleted the 5' end of the coding region to the Nco I site. This was designated pNN39.

B. Chimeric Receptors (1) hNPY5 Y1IC3 (SEQ ID NO: 5)

For the IC loop 3 chimera, pNN39 was digested with PstI (located at about residues 748–753 of human Y5 receptor sequence (SEQ ID NO: 6) and Bgl II (located at about residues 1130–1135 of the human Y5 receptor sequence) removing bases 753 to 1130.

The portion of IC loop 3 from bases 903–964 (TACGCCTAAAAAGGAGAAACAACATGATGGACAAGATGAGAGACAATAAG TACAGGTCCAGT; SEQ ID NO: 8) of human Y5 receptor, corresponding to amino acids 236–256 (IRLKRRNNMMDKMRDNKYRSS; SEQ ID NO: 9) of the human Y5 receptor amino acid sequence, was inserted into Y5 using the HY1L3S sense oligo (SEQ ID NO: 10) and the HY1L3AS antisense oligo (SEQ ID NO: 11). A reaction mixture containing the 2 oligos was heated to 100° C. and allowed to cool slowly to anneal the oligos. The double stranded annealing product was then ligated into the PstI-Bgl II digested pNN39 to yield plasmid pNN100. The pNN100 insert was then reintroduced into the full-length human Y5 gene (pNN32) at the Cel 2 site and the resulting plasmid was designated pNN42.

(2) hNPY5 Y1CT (SEQ ID NO: 12)

To add the Y1 C-terminus to Y5, an Eco RI site was added to each gene. For Y1, bases 1173 to 1178 (ACTTCC) of human Y1 receptor (SEQ ID NO: 3) were mutated to create an Eco R1 site via PCR from forward primer HY1R1 (SEQ ID NO: 13) to a T3 reverse primer priming from the multiple cloning site—"MCS"—of pBSSKM). The Y1 3' tail was then isolated by digesting with Eco RI and Xba (which later enzyme cuts out the Y1 3' tail in the MCS of pBSSKM).

For Y5, bases 1338 to 1343 (GGATTA) of human Y5 receptor were mutated using the PCR reverse primer HY5R1 (SEQ ID NO: 14). This primer was paired with a forward primer corresponding to bases 527–551 (GCTACTGTCTGGACACTAGGTTTTG; SEQ ID NO: 15) of human Y5 receptor, and PCR carried out with the human Y5 coding sequence as template. The resulting PCR band was cut Pst I to the introduced Eco RI site.

pNN39 was then opened Pst I to Xba from the MCS of pBSSKM and the mutated Y5 segment PstI to Eco RI was mixed with the mutated Y1 3' fragment Eco RI to Xba from the MCS to set up a three-way ligation. The resulting mutated gene fragment was then introduced into the full-length Y5 gene at the Bgl 2 site.

(3) hNPY5 Y1IC$_3$/Y1CT (SEQ ID NO: 16)

The IC loop 3+CT tail exchange was obtained by combining the above 2 mutant genes in the following manner. Full length hY5 (pNN32) was digested with Cel 2 (located at about residues 619–625 of human Y5 receptor) and Xba in the vector MCS. The loop 3 mutation pNN42 fragment Cel II to Bgl II was combined with the CT mutation pNN43 fragment Bgl II to Xba from the MCS resulting in pNN44. pNN44 encodes a human chimeric $NPY_5/NPY_1$ NPY receptor, consisting of N-terminal amino acids 1–442 of the human $NPY_5$ receptor and C-terminal amino acids 328–384 of the human $NPY_1$ receptor. The amino acid sequence of this chimeric receptor, referred to herein as hNPY5 Y1IC3/Y1CT is shown in SEQ ID NO17:).

PNN44 was then digested with Kpn I and Xba I and subcloned into the commercial expression vector pBacPAK9 (Clontech, Palo Alto, Calif.) for expression in SF9 cells.

C. Baculoviral Preparations

The Baculoviral expression vector was co-transfected along with BACULOGOLD DNA (BD PharMingen, San Diego, Calif.) into Sf9 cells. The Sf9 cell culture supernatant was harvested three days post-transfection. The recombinant virus-containing supernatant was serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques were selected and harvested into 1 ml of insect medium for amplification. Each 1 ml volume of recombinant baculovirus (at passage 0) was used to infect a separate T25 flask containing 2×10⁶ Sf9 cells in 5 mls of insect medium. After five days of incubation at 27° C., supernatant medium was harvested from each of the T25 infections for use as passage 1 inoculum. Two of the seven recombinant baculoviral clones were then chosen for a second round of amplification, using 1 ml of passage 1 stock to infect 1×10⁸ cells in 100 ml of insect medium divided into 2 T175 flasks. Forty-eight hours post infection, passage 2 medium from each 100 ml prep was harvested and plaque assayed for titer. The cell pellets from the second round of amplification were assayed by affinity binding as described below to verify recombinant receptor expression. A third round of amplification was then initiated using an M.O.I. of 0.1 to infect a liter of Sf9 cells. Forty hours post-infection the supernatant medium was harvested to yield passage 3 baculoviral stock and the cell pellet assayed for affinity binding. Titer of the passage 3 baculoviral stock was determined by plaque assay and an M.O.I. and Incubation Time Course experiment was carried out to determine conditions for optimal receptor expression. Results from the receptor optimization experiment show that an M.O.I. of 0.1 and a 72 hour incubation were the ideal infection parameters in order to achieve optimum Y5 receptor expression in up to 1 liter Sf9 cell infection cultures.

Log-phase Sf9 cells infected with recombinant baculovirus encoding the human chimeric $NPY_5/NPY_1$ NPY receptor designated hNPY5 Y1IC3/Y1CT, above, were cultured in insect medium at 27° C. 72 hours post-infection, a sample of cell suspension was analyzed for viability by trypan blue dye exclusion, and the remaining Sf9 cells were harvested via centrifugation (3000 rpm/10 minutes/4° C.).

Example 11

Assay for NPY5 Receptor Binding Activity

This Example illustrates the measurement of binding activity for representative compounds.

The baculovirus-infected Sf9 cells expressing recombinant human chimeric NPY5/NPY1 receptor, as described in Example 10, were harvested at 42–48 hours at which time batches of 500 mL of cell suspension were pelleted by centrifugation. Each pellet was re-suspended in 30 mL of homogenization buffer (10 mM HEPES, 250 mM sucrose, 0.5 μg/mL leupeptin, 2 μg/mL Aprotonin, 200 μM PMSF and 2.5 mM EDTA, pH 7.4) and homogenized using a POLYTRON homogenizer (setting 5 for 30 seconds). The homogenate was centrifuged at 4° C. for 10 minutes at 536×g to pellet the nuclei. The supernatant containing isolated membranes was decanted into a clean centrifuge tube, centrifuged in the same buffer at 48,000×g for 30 minutes at 4° C. and resuspended in 30 ml homogenization buffer. This centrifugation and resuspension step was repeated twice. The final pellet was re-suspended in ice cold Dulbecco's PBS containing 5 mM EDTA, and stored in frozen aliquots at −80° C. The protein concentration of the resulting membrane preparation (P2 preparation) was measured using the Bradford protein assay (Bio-Rad Laboratories, Hercules, Calif.). By this measure, a 1-liter culture of cells typically yields 50–75 mg of total membrane protein.

Purified P2 membranes were thawed, centrifuged and washed by PBS and re-suspended by Dounce homogenization (tight pestle) in binding buffer (50 mM Tris(HCl), 5 mM KCl, 120 mM NaCl, 2 mM $CaCl_2$, 1 mM $MgCl_2$, 0.1% bovine serum albumin (BSA), pH 7.4). For competition analysis, membranes (5–50 μg) were added to polypropylene tubes containing 0.050 nM [¹²⁵I]PYY(porcine) and 2 μl test compound in DMSO (1 μM–4 μM final concentration). For saturation binding analysis, membranes (5–50 μg) were added to polypropylene tubes containing 0.010–0.500 nM [¹²⁵I]PYY (porcine; New England Nuclear Corp., Boston, Mass.). Nonspecific binding was determined in the presence of 1 μM NPY (human; American Peptide Co., Sunnyvale, Calif.) and accounted for less than 10% of total binding. Following a 2 hour incubation at room temperature, the reaction was terminated by rapid vacuum filtration. Samples were filtered over presoaked (in 1.0% polyethyleneimine for 2 hours prior to use) GF/C WHATMAN filters and rinsed 2 times with 5 mL cold binding buffer without BSA. Remaining bound radioactivity was measured by gamma counting. $K_i$ and Hill coefficient ("nH") were determined by fitting the Hill equation to the measured values with the aid of SIGMAPLOT software (SPSS Inc., Chicago). The binding affinity for the compounds provided herein, expressed as a Ki value, ranged from about 0.1 nanomolar to about 10 micromolar. The most active of these compounds have a Ki of less than 100 nanomolar.

Example 12

Calcium Mobilization Assay for Determining NPY5 Receptor Modulation

This Example illustrates a representative assay for evaluating the effect of compounds on NPY5 receptor signal transduction.

Bowes Melanoma cells stably transfected with an expression vector encoding the NPY5/NPY1 chimeric receptor described above were plated at a density of 26,000 cells/well in FALCON black-walled, clear-bottomed 96-well plates (#3904, BECTON-DICKINSON, Franklin Lakes, N.J.) and grown to confluency, approximately 24 hours. The culture medium was emptied from the 96 well plate, and Fluo-3 calcium sensitive dye (Molecular Probes, Eugene, Oreg.) was added to each well (dye solution: 1 mg FLUO-3 AM, 440 μL DMSO and 440 μl 20% pluronic acid in DMSO, diluted 1:2, 50 ul diluted solution per well). Plates were covered with aluminum foil and incubated at 37 C. for 1–2 hours. After the incubation, the dye solution was emptied from the plates, cells were washed once in 100 μl KRH buffer (0.05 mM KCl, 0.115 M NaCl, 9.6 mM $NaH_2PO_4$, 0.01 mM $MgSO_4$, 25 mM HEPES, pH 7.4) to remove excess dye. After washing, 80 μl KRH buffer with carbachol/Thomae (KRH buffer containing 1 mM carbachol, 10 micromolar BIBP 3226 (Sigma RBI, St. Louis Mo.)) was added to each well. Assay plates were incubated in the dark, 20 minutes.

To measure the ability of a test compound to antagonize the response of cells expressing NPY5 receptor to NPY, the $EC_{50}$ of NPY was first determined. An additional 20 μl of KRH/Thomae buffer and 1 μl DMSO was added to each well of cells, prepared as described above. 100 μl human NPY in KRH/Thomae buffer was automatically transferred by the FLIPR instrument to each well. An 8-point concentration response curve, with final NPY concentrations of 1 nM to 3 μM, was used to determine NPY $EC_{50}$.

Test compounds were dissolved in 1 μl DMSO, diluted in 20 μl KRH buffer with carbachol/Thomae, and added to cells prepared as described above. The 96 well plates containing prepared cells and test compounds were incubated in the dark, at room temperature for 0.5–6 hours. It is important that the incubation not continue beyond 6 hours. Just prior to determining the fluorescence response, 100 μl human NPY diluted in KRL/Thomae buffer to 2×$EC_{50}$ was automatically added by the FLIPR instrument to each well of the 96 well plate for a final sample volume of 200 µl and a final NPY concentration of $EC_{50}$. The final concentration of test compounds in the assay wells was between 1 µM and 5 µM. Typically cells exposed to one $EC_{50}$ of NPY exhibit a fluorescence response of about 10,000 Relative Fluorescence Units. Antagonists of the NPY5 receptor exhibit a response that is significantly less than that of the control cells to the p 0.05 level, as measured using a parametric test of statistical significance. Typically, antagonists of the NPY5 receptor decrease the fluorescence response relative to control cells by about 20%, preferably by about 50%, and most preferably by at least 80% as compared to matched control.

Example 13

Antagonism of Bovine Pancreatic Polypeptide-Induced Food Intake

This Example illustrates the use of representative compounds to decrease food intake.

Male Sprague-Dawley rats aged 7 weeks are maintained under controlled temperature (23±3° C.), humidity (55±15%) and light-dark cycle (7:00–19:00 light on). Rats are housed individually with ad libitum access to food and water.

Rats are anesthetized with sodium pentobarbital (50 mg/kg, i.p.). A permanent stainless steel guide cannula for intracerebroventricular (ICV) injection (21 gauge, 10 mm long) is stereotaxically implanted into the right lateral ventricle. The stereotaxic coordinates used are as follows: 0.9 mm posterior and 1.2 mm lateral to the bregma and 0.5 mm ventral to the brain surface.

Animals are allowed to recover at least 6 days postoperatively before the start of the feeding experiment. The day before the experiment, animals are handled and undergo mock injection, and nocturnal food intake is measured. Rats that eat more than 15 g during the night before the experiment are used for the BPP feeding antagonism experiment.

Test compounds are suspended in 0.5% methylcellulose and orally administered by gavage. Administration of test compounds usually begins at 10:00. Dosing volume is about 5 ml/kg. One hour after administration of the test compound, bovine pancreatic polypeptide (Bovine PP 5 µg/10 µl/1 min.) is injected ICV through a stainless steel injector (26 gauge) attached to a 50 µl Hamilton microsyringe by polyethylene tubing. Bovine PP is dissolved in 10 mM PBS containing 0.05% BSA. Two hour post-injection food intake is measured for each rat.

Test compounds that reduce food intake two hours post-injection relative to food intake of control animals (animals inject with Bovine PP but not a test compound) are identified as compounds that antagonize bovine PP induced feeding.

Example 14

Food Deprivation Model

This Example illustrates the use of representative NPY5 modulators to decrease food intake within a food deprivation model.

Experimentally naive and experienced male Sprague-Dawley rats (Sasco, St. Louis, Mo.) weighing 210–300 g at the beginning of the experiment are used. Animals are triple-housed in stainless steel hanging cages in a temperature (22 C.±2) and humidity (40–70% RH) controlled animal facility with a 12:12 hour light-dark cycle. Food (Standard Rat Chow, PMI Feeds Inc., #5012) and water are available ad libitum.

Consumption data is collected while the animals were housed in Nalgene Metabolic cages (Model #650–0100). Each cage is comprised of subassemblies made of clear polymethlypentene (PMP), polycarbonate (PC), or stainless steel (SS). All parts disassemble for quick and accurate data collection and for cleaning. The entire cylinder-shaped plastic and SS cage rests on a SS stand and houses one animal.

The animal is contained in the round Upper Chamber (PC) assembly (12 cm high and 20 cm in diameter) and rests on a SS floor. Two subassemblies are attached to the Upper Chamber. The first assembly consists of a SS feeding chamber (10 cm long, 5 cm high and 5 cm wide) with a PC feeding drawer attached to the bottom. The feeding drawer has two compartments: a food storage compartment with the capacity for approximately 50 g of pulverized rat chow, and a food spillage compartment. The animal is allowed access to the pulverized chow by an opening in the SS floor of the feeding chamber. The floor of the feeding chamber does not allow access to the food dropped into the spillage compartment. The second assembly includes a water bottle support, a PC water bottle (100 ml capacity) and a graduated water spillage collection tube. The water bottle support funnels any spilled water into the water spillage collection tube.

The lower chamber consists of a PMP separating cone, PMP collection funnel, PMP fluid (urine) collection tube, and a PMP solid (feces) collection tube. The separating cone is attached to the top of the collection funnel, which in turn is attached to the bottom of the Upper Chamber. The urine runs off the separating cone onto the walls of the collection funnel and into the urine collection tube. The separating cone also separates the feces and funnels it into the feces collection tube. Food consumption, water consumption, and body weight were measured with an Ohaus Portable Advanced scale (±0.1 g accuracy).

Prior to the day of testing, animals were habituated to the testing apparatus by placing each animal in a Metabolic cage for 1 hour. On the day of the experiment, animals that were food deprived the previous night were weighed and assigned to treatment groups. Assignments were made using a quasi-random method utilizing the body weights to assure that the treatment groups had similar average body weight. Animals were then administered either vehicle (0.5% methyl cellulose, MC) or NPY5 modulator. At that time, the feeding drawer filled with pulverized chow, the filled water bottle, and the empty urine and feces collection tubes were weighed. Two hours after modulator treatment, each animal is weighed and placed in a Metabolic Cage. Following a one hour test session, animals are removed and body weight obtained. The food and water containers are then weighed and the data recorded.

NPY5 modulators (suspended in 0.5% MC) or 0.5% MC are administered orally (PO) using a gavage tube connected to a 3 or 5 ml syringe at a volume of 10 ml/kg. Each modulator was made into a homogenous suspension by stirring and ultrasonicating for at least 1 hour prior to dosing.

The means and standard errors of the mean (SEM) for food consumption, water consumption, and body weight change are presented. One-way analysis of variance using Systat (5.2.1) was used to test for group differences. A significant effect is defined as having a p value of <0.05.

The following parameters are defined: Body weight change is the difference between the body weight of the animal immediately prior to placement in the metabolic cage and its body weight at the end of the one hour test session.

Food consumption is the difference in the weight of the food drawer prior to testing and the weight following the 1 hour test session. Water consumption is the difference in the weight of the water bottle prior to testing and the weight following the 1 hour test session. The most potent compounds of the invention significantly reduce food intake and body weight gain.

Description of the Sequence Listing

SEQ ID NO: 1 is a 5' human NPY5 receptor primer
SEQ ID NO: 2 is a 3' human NPY5 receptor primer
SEQ ID NO: 3 is human NPY1 receptor
SEQ ID NO: 4 is NPY1 amino acid sequence
SEQ ID NO: 5 is the chimeric DNA sequence designated hNPY5 Y1IC3
SEQ ID NO: 6 is human NPY5 receptor nucleotide sequence
SEQ ID NO: 7 is human NPY5 receptor amino acid sequence
SEQ ID NO: 8 is nucleotides 903–964 of human NPY5 receptor
SEQ ID NO: 9 is amino acids 236–256 of human NPY5 receptor
SEQ ID NO: 10 is the HY1L3S sense oligo
SEQ ID NO: 11 is HY1L3AS antisense oligo
SEQ ID NO: 12 is the chimeric DNA sequence designated hNPY5 Y1CT
SEQ ID NO: 13 is primer HY1R1
SEQ ID NO: 14 is primer HY5R1
SEQ ID NO: 15 is forward primer corresponding to bases 527–551 of humany 5 receptor
SEQ ID NO: 16 is the chimeric DNA sequence designated hNPY5 Y1IC3/Y1CT
SEQ ID NO: 17 is amino acid sequence of the chimeric receptor hNPY5 Y1IC3/Y1CT From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound of the formula:

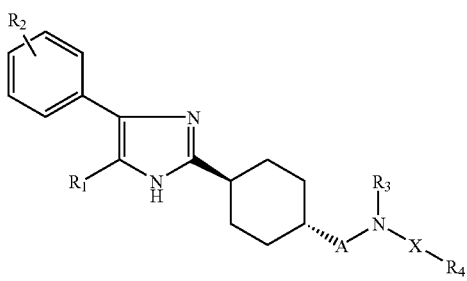

Formula I or a pharmaceutically acceptable salt thereof, wherein:

$R_1$ represents hydrogen, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_2$–$C_8$ carbonate, $C_2$–$C_8$ carbamate, $C_1$–$C_8$ alkylthio, halo($C_1$–$C_8$)alkyl, halo($C_1$–$C_8$)alkoxy, hydroxy($C_1$–$C_8$)alkyl, hydroxy($C_1$–$C_8$)alkoxy, mono or di($C_1$–$C_8$)alkyl amino, $C_1$–$C_8$ alkanoyl, $C_1$–$C_8$ alkoxycarbonyl, —COOH, —SO$_2$NH$_2$, mono or dialkylsulfonamido, —C(O)NH$_2$ or mono or di($C_1$–$C_8$)alkylcarboxamido;

$R_2$ represents 0 to 5 ring substituents, each substituent independently selected from hydrogen, halogen, hydroxyl, amino, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_2$–$C_8$ carbonate, $C_2$–$C_8$ carbamate, $C_1$–$C_8$ alkylthio, halo($C_1$–$C_8$)alkyl, halo($C_1$–$C_8$)alkoxy, hydroxy($C_1$–$C_8$)alkyl, hydroxy($C_1$–$C_8$)alkoxy, mono or di($C_1$–$C_8$)alkyl amino, $C_1$–$C_8$ alkanoyl, $C_1$–$C_8$ alkoxycarbonyl, —COOH, —SO$_2$NH$_2$, mono and dialkylsulfonamido, —C(O)NH$_2$, and mono and di($C_1$–$C_8$)alkylcarboxamido;

A represents —CO— or —(CH$_2$)$_n$—, wherein n is an integer ranging from 1 to 3;

$R_3$ represents:

(i) hydrogen;

(ii) $C_1$–$C_8$ alkyl, optionally substituted with from 1 to 8 substituents that are independently selected from halogen, hydroxyl, carbocyclic groups and heterocyclic groups, wherein each carbocyclic or heterocyclic group contains from 3 to 10 ring members; or (iii) a bond to $R_4$, forming a heterocyclic group having from 1 to 3 fused or pendant rings, each ring containing from 5 to 10 ring members, wherein each ring is optionally substituted by from 1 to 5 substituents that are independently selected from halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, hydroxy, amino, mono or di($C_1$–$C_8$)alkyl amino, halo($C_1$–$C_8$)alkyl, halo($C_1$–$C_8$)alkoxy, hydroxy($C_1$–$C_8$)alkyl, hydroxy ($C_1$–$C_8$)alkoxy $C_2$–$C_8$ alkanoyl, $C_1$–$C_8$ alkoxycarbonyl, —COOH, —$SO_2NH_2$, mono or dialkylsulfonamido, —C(O)$NH_2$ and mono and di($C_1$–$C_8$) alkylcarboxamido;

X represents a bond, —S(O)$_2$—, —C(O)— or —NHC(O)—; and $R_4$:
(i) represents hydrogen;
(ii) represents $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_2$–$C_8$ carbonate, halo($C_1$–$C_8$)alkyl, halo($C_1$–$C_8$)alkoxy, hydroxy($C_1$–$C_8$)alkyl, hydroxy($C_1$–$C_8$)alkoxy, $C_2$–$C_8$ alkanone or $C_1$–$C_8$ alkyl ether, optionally substituted with from 1 to five substituents that are independently selected from halogen, hydroxyl, carbocyclic groups and heterocyclic groups, wherein each carbocyclic or heterocyclic group contains from 5 to 10 ring members;
(iii) represents a carbocyclic or heterocyclic group having from 1 to 3 fused or pendant rings, each ring containing from 5 to 10 ring members, wherein each ring is optionally substituted by from 1 to 5 substituents that are independently selected from halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_2$–$C_8$ carbonate, $C_2$–$C_8$ carbamate, $C_2$–$C_6$ alkanone, $C_2$–$C_6$ alkyl ether, $C_1$–$C_8$ alkylthio, hydroxy, amino, mono or di($C_1$–$C_8$)alkyl amino, halo($C_1$–$C_8$)alkyl, halo($C_1$–$C_8$)alkoxy, hydroxy($C_1$–$C_8$)alkyl, hydroxy ($C_1$–$C_8$)alkoxy $C_2$–$C_8$ alkanoyl, $C_1$–$C_8$ alkoxycarbonyl, —COOH, —$SO_2NH_2$, mono or dialkylsulfonamido, —C(O)$NH_2$ and mono or di($C_1$–$C_8$)alkylcarboxamido; or
(iv) taken together with $R_3$ and X, represents a heterocyclic group having from 1 to 3 fused or pendant rings, each ring containing from 5 to 10 ring members, wherein each ring is optionally substituted by from 1 to 5 substituents that are independently selected from halogen, cyano, nitro, $C_1$–$C_8$ alkyl, $C_2$–$C_8$ alkenyl, $C_2$–$C_8$ alkynyl, $C_1$–$C_8$ alkoxy, $C_1$–$C_8$ alkanoyloxy, $C_2$–$C_8$ carbonate, $C_2$–$C_8$ carbamate, $C_1$–$C_8$ alkylthio, hydroxy, amino, mono or di($C_1$–$C_8$)alkyl amino, halo($C_1$–$C_8$)alkyl, halo($C_1$–$C_8$)alkoxy, hydroxy($C_1$–$C_8$)alkyl, hydroxy ($C_1$–$C_8$)alkoxy $C_2$–$C_8$ alkanoyl, $C_1$–$C_8$ alkoxycarbonyl, COOH, —$SO_2NH_2$, mono or dialkylsulfonamido, —C(O)$NH_2$ and mono or di($C_1$–$C_8$)alkylcarboxamido.

2. A compound according to claim 1, wherein the compound further satisfies Formula II.

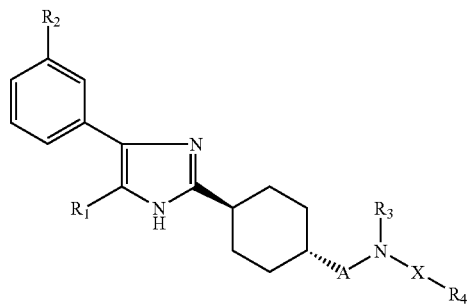

Formula II

3. A compound according to claim 1, wherein $R_3$ is hydrogen, methyl, ethyl or propyl.

4. A compound according to claim 1, wherein $R_4$ is:
(i) an aromatic group selected from phenyl, benzyl, phenoxyl, benzoxyl, phenylethanonyl, pyrimidin-2-yl, pyrimidin-4-yl, pyrimidin-5-yl, tetrahydropyran-2-yl, indan-1-yl, tetrazolyl, pyridin-2-yl, pyridin-3-yl and pyridin-4-yl, wherein the group is optionally substituted by from 1 to 3 substituents independently selected from hydroxyl, halogen and $C_1$–$C_6$ alkyl;
(ii) a non-aromatic group selected from hydrogen, $C_1$–$C_6$ alkyl, $C_1$–$C_6$ alkoxyl, halo($C_1$–$C_6$)alkyl, halo($C_1$–$C_6$) alkoxyl, hydroxy($C_1$–$C_6$)alkyl, hydroxy($C_1$–$C_6$) alkoxyl, $C_2$–$C_6$ alkanone or $C_1$–$C_6$ alkyl ether; or
(iii) taken with $R_3$ and X to form a heterocyclic group selected from tetrazolyl, morpholin-4-yl, pyrimidin-2-yl, pyridin-2-yl, pyridin-3-yl and pyridin-4-yl, piperdin-1-yl, pyrrolidin-1-yl, each of which is optionally substituted with from 1 to 3 substituents independently selected from halogen, $C_1$–$C_6$ alkyl, $C_1$–$C_6$ alkoxyl, hydroxyl, halo($C_1$–$C_6$)alkyl and halo($C_1$–$C_6$)alkoxyl.

5. A compound according to claim 1, wherein A is —$CH_2$—.

6. A compound according to claim 1, wherein X is —S(O)$_2$—, $R_3$ is hydrogen and $R_4$ is a group selected from phenyl, pyridyl and pyrimidyl, wherein the group is optionally substituted by from 1 to 3 substituents independently selected from hydroxyl, halogen and $C_1$–$C_6$ alkyl.

7. A compound according to claim 1, wherein A is —$CH_2$—, X is —C(O)—, $R_3$ is hydrogen and $R_4$ is $C_1$–$C_6$ alkyl, $C_1$–$C_6$ alkoxyl, halo($C_1$–$C_6$)alkyl or halo($C_1$–$C_6$) alkoxyl.

8. A compound according to claim 1, wherein A is —C(O)—, X is —NHC(O)—, $R_3$ is hydrogen and $R_4$ is $C_1$–$C_6$ alkyl.

9. A compound according to claim 1, wherein A is —C(O)—, X is a bond, $R_3$ is hydrogen or $C_1$–$C_6$ alkyl, and $R_4$ is $C_1$–$C_6$ alkyl, halo($C_1$–$C_6$)alkyl, hydroxy($C_1$–$C_6$)alkyl, or an aromatic group selected from phenyl, pyrimidin-2-yl, indan-1-yl, wherein the group is optionally substituted by from 1 to 3 substituents independently selected from hydroxyl, halogen, $C_1$–$C_6$ alkyl, hydroxy($C_1$–$C_6$)alkyl and $C_2$–$C_6$ alkanone.

10. A compound according to claim 1, wherein the compound is selected from:
- (a) 2-Chloro-N-{4-[4-(3-trifluoromethyl-phenyl)-1H-imidazol-2-yl]cyclohexanecarbonyl}-benzene sulfonamide;
- (b) 4-[4-(3-Trifluoromethyl-phenyl)-1H-imidazol-2-yl]-cyclohexanecarboxylic acid(2-hydroxy-propyl)-methyl-amide;
- (c) 4-[4-(3-Trifluoromethyl-phenyl)-1H-imidazol-2-yl]-cyclohexanecarboxylic acid(2-oxo-2-phenyl-ethyl)-amide;
- (d) Pyridine-3-sulfonic acid{4-[4-(3-trifluoromethyl-phenyl)-1H-imidazol-2-yl]-cyclohexylmethyl}-amide;
- (e) 4-[4-(3-Trifluoromethyl-phenyl)-1H-imidazol-2-yl]-cyclohexanecarboxylic acid(2-hydroxy-2-phenyl-ethyl)-amide;
- (f) 1-{4-[4-(3-Trifluoromethyl-phenyl)-1H-imidazol-2-yl]-cyclohexylmethyl}-1H-tetrazole;
- (g) N-{4-[4-(3-Trifluoromethyl-phenyl)-1H-imidazol-2-yl]-cyclohexylmethyl}-benzenesulfonamide;
- (h) 4-[4-(3-Trifluoromethyl-phenyl)-1H-imidazol-2-yl]-cyclohexanecarboxylic acid(2-hydroxy-indan-1-yl)-amide;
- (i) {4-[4-(3-Chloro-phenyl)-1H-imidazol-2-yl]-cyclohexylmethyl}-carbamic acid ethyl ester;
- (j) Cyclopentyl-{4-[4-(3-trifluoromethyl-phenyl)-1H-imidazol-2-yl]-cyclohexylmethyl}-amine;
- (k) N-{4-[4-(4-Bromo-phenyl)-1H-imidazol-2-yl]-cyclohexylmethyl}-2,2,2-trifluoro-acetamide;
- (l) N-{4-[4-(3-trifluoromethyl-phenyl)-1H-imidazol-2-yl]-cyclohexanecarbonyl}-benzene sulfonamide;
- (m) Pyrimidin-2-yl-{4-[4-(3-trifluoromethyl-phenyl)-1H-imidazol-2-yl]-cyclohexylmethyl}-amine;
- (n) 4-[4-(3-Bromo-phenyl)-1H-imidazol-2-yl]-cyclohexanecarboxylic acid N-acetyl-hydrazide;
- (o) 4,N-Dimethyl-N-{4-[4-(3-trifluoromethyl-phenyl)-1H-imidazol-2-yl]-cyclohexanecarbonyl}-benzene sulfonamide;
- (p) N-{4-[4-(3-Trifluoromethyl-phenyl)-1H-imidazol-2-yl]-cyclohexylmethyl}-acetamide;
- (q) Benzenesulfinic acid {4-[4-(3-chloro-phenyl)-1H-imidazol-2-yl]-cyclohexylmethyl}-amide;
- (r) 4-[4-(3-Trifluoromethyl-phenyl)-1H-imidazol-2-yl]-cyclohexanecarboxylic acid(2-hydroxy-1,1-dimethyl-ethyl)-amide;
- (s) 4-Hydroxy-N-{4-[4-(3-trifluoromethyl-phenyl)-1H-imidazol-2-yl]-cyclohexylmethyl}-butyramide;
- (t) 4-methyl-N-{4-[4-(3-trifluoromethyl-phenyl)-1H-imidazol-2-yl]-cyclohexanecarbonyl}-benzene sulfonamide;
- (u) N-{4-[4-(3-Bromo-phenyl)-1H-imidazol-2-yl]-cyclohexylmethyl}-trifluoroacetamide;
- (v) 4-[4-(3-Trifluoromethyl-phenyl)-1H-imidazol-2-yl]-cyclohexanecarboxylic acid (2-hydroxy-propyl)-amide;
- (w) N-{4-[5-methyl-4-(3-trifluoromethyl-phenyl)-1H-imidazol-2-yl]-cyclohexylmethyl}-acetamide;
- (x) 2,2,2-Trifluoro-N-{4-[4-(4-methoxy-phenyl)-1H-imidazol-2-yl]-cyclohexylmethyl}-acetamide;
- (y) 4-Chloro-N-{4-[4-(3-trifluoromethyl-phenyl)-1H-imidazol-2-yl]-cyclohexanecarbonyl}-benzene sulfonamide;
- (aa) 4-[4-(3-Bromo-phenyl)-1H-imidazol-2-yl]-cyclohexanecarboxylic acid pyrimidin-2-ylamide;
- (bb) N-Methyl-N-{4-[4-(3-trifluoromethyl-phenyl)-1H-imidazol-2-yl]-cyclohexylmethyl}-benzenesulfonamide;
- (cc) N-{4-[4-(3-Bromo-phenyl)-1H-imidazol-2-yl]-cyclohexylmethyl}-acetamide;
- (dd) 5-Methyl-pyridine-2-sulfonic acid {4-[4-(3-trifluoromethyl-phenyl)-1H-imidazol-2-yl]-cyclohexanecarbonyl}-amide;
- (ee) 4-[4-(3-Trifluoromethyl-phenyl)-1H-imidazol-2-yl]-cyclohexanecarboxylic acid (1-hydroxymethyl-2-methyl-propyl)-amide;
- (ff) {4-[5-Methyl-4-(3-trifluoromethyl-phenyl)-1H-imidazol-2-yl]-cyclohexylmethyl}-carbamic acid benzyl ester;
- (hh) 4-[4-(3-Trifluoromethyl-phenyl)-1H-imidazol-2-yl]-cyclohexanecarboxylic acid N-acetyl-hydrazide;
- (ii) 2,2,2-Trifluoro-N-{4-[4-(4-phenyl-1H-imidazol-2-yl]-cyclohexylmethyl}-acetamide; and
- (jj) 2,2,2-Trifluoro-N-{4-[4-(3-trifluoromethyl-phenyl)-1H-imidazol-2-yl]-cyclohexylmethyl}-acetamide.

11. A compound according to claim 1, wherein the compound exhibits a $K_i$ of 1 micromolar or less in an NPY5 receptor ligand binding assay.

12. A compound according to claim 1, wherein the compound exhibits a $K_i$ of 100 nanomolar or less in an NPY5 receptor ligand binding assay.

13. A compound according to claim 1, wherein the compound exhibits a $K_i$ of 10 nanomolar or less in an NPY5 receptor ligand binding assay.

14. A compound according to claim 1, wherein the compound is an NPY5 receptor modulator.

15. A pharmaceutical composition comprising a compound according to claim 1 or a modulator according to claim 14 in combination with a physiologically acceptable carrier or excipient.

16. A pharmaceutical composition according to claim 15, wherein the composition is formulated as an injectible fluid, an aerosol, a cream, a gel, a pill, a capsule, a syrup or a transdermal patch.

17. A packaged pharmaceutical preparation, comprising: (a) a pharmaceutical composition according to claim 15 in a container; and (b) instructions for using the composition to treat a patient suffering from a disorder responsive to NPY-5 receptor antagonism or agonism.

18. A packaged pharmaceutical preparation according to claim 17, wherein the patient is suffering from an eating disorder, a psychiatric disorder, a cardiovascular disorder or diabetes.

* * * * *

UNITED STATES PATENT AND TRADEMARK OFFICE
CERTIFICATE OF CORRECTION

PATENT NO. : 7,034,034 B2
APPLICATION NO. : 10/271851
DATED : April 25, 2006
INVENTOR(S) : Blum et al.

Page 1 of 1

It is certified that error appears in the above-identified patent and that said Letters Patent is hereby corrected as shown below:

Claim 2, column 64, line 2: delete "." and insert -- : --

Claim 2, column 64, line 20: insert -- and wherein $R_2$ is trifluoromethyl, halogen or cyano. --

Summary of Invention, column 2, line 38: delete "13"

NPY5 Receptor Modulators, column 19, line 45: delete "NPY," and insert -- $NPY_1$ --

Example 10, column 40, line 18, between "primer" and "priming": insert -- ( --

Signed and Sealed this

Twenty-second Day of August, 2006

JON W. DUDAS
*Director of the United States Patent and Trademark Office*